(12) United States Patent
Kalesse et al.

(10) Patent No.: US 9,458,200 B2
(45) Date of Patent: Oct. 4, 2016

(54) METHOD FOR PRODUCING INTERMEDIATES FOR THE PRODUCTION OF NOVEL MACROCYCLES THAT ARE INHIBITORS OF THE PROTEASOMIC DEGRADATION OF P27, SUCH AS ARGYRIN AND DERIVATIVES THEREOF, AND USES OF SAID MACROCYCLES

(75) Inventors: Markus Kalesse, Burgdorf (DE); Nisar Malek, Hannover (DE); Ronald Frank, Meine (DE); Tobias Brodmann, Hannover (DE); Leila Bülow, Hannover (DE); Andreas Rentsch, Hannover (DE); Anna-Katharina Girbig, Hannover (DE); Ulrike Eggert, Hannover (DE)

(73) Assignees: Gottfried Wilhelm Leibniz Universität Hannover, Hannover (DE); Medizinische Hochschule Hannover, Hannover (DE); Helmholtz-Zentrum für Infektionsforschung GmbH, Braunschweig (DE)

( * ) Notice: Subject to any disclaimer, the term of this patent is extended or adjusted under 35 U.S.C. 154(b) by 420 days.

(21) Appl. No.: 13/000,516

(22) PCT Filed: Jun. 23, 2009

(86) PCT No.: PCT/EP2009/004526
§ 371 (c)(1),
(2), (4) Date: May 31, 2011

(87) PCT Pub. No.: WO2010/006682
PCT Pub. Date: Jan. 21, 2010

(65) Prior Publication Data
US 2011/0311564 A1    Dec. 22, 2011

(30) Foreign Application Priority Data
Jun. 23, 2008   (EP) .................................. 08011346

(51) Int. Cl.
C07K 7/56 (2006.01)
A61K 38/00 (2006.01)
(52) U.S. Cl.
CPC ........ *C07K 7/56* (2013.01); *A61K 38/00* (2013.01)
(58) Field of Classification Search
None
See application file for complete search history.

(56) References Cited

FOREIGN PATENT DOCUMENTS

| EP | 1 964 560 A1 | 9/2008 |
|---|---|---|
| GB | 2 367 553 A | 4/2002 |

OTHER PUBLICATIONS

White et al ('Contemporary strategies for peptide macrocyclization' Nature Chemistry v3 Jul. 2011 pp. 509-524).*
Ley et al., "Total Synthesis of the Cyclic Heptapeptide Argyrin B: A New Potent Inhibitor of T-Cell Independent Antibody Formation", *Organic Letters*, 2002, vol. 4, No. 5, pp. 711-714.
Ley et al., "Total Synthesis of the Cyclic Peptide Argyrin B", *European Journal of Organic Chemistry*, 2002, vol. 2002, No. 23, pp. 3995-4004.
Sasse et al., "Argyrins, Immunosuppressive Cyclic Peptides from Myxobacteria", *The Journal of Antibiotics*, Jun. 2002, vol. 55, No. 6, pp. 543-551.

* cited by examiner

*Primary Examiner* — Christina Bradley
*Assistant Examiner* — Ronald Niebauer
(74) *Attorney, Agent, or Firm* — Saliwanchik, Lloyd & Eisenschenk

(57) ABSTRACT

The present invention relates to the use of particular macrocycles that are inhibitors of the proteasomic degradation of p27, in particular argyrin and derivatives thereof, for a treatment in a variety of conditions, such as the induction of immunotolerance, autoimmune diseases, bacterial infections, and proliferative diseases, such as cancers.

5 Claims, 4 Drawing Sheets

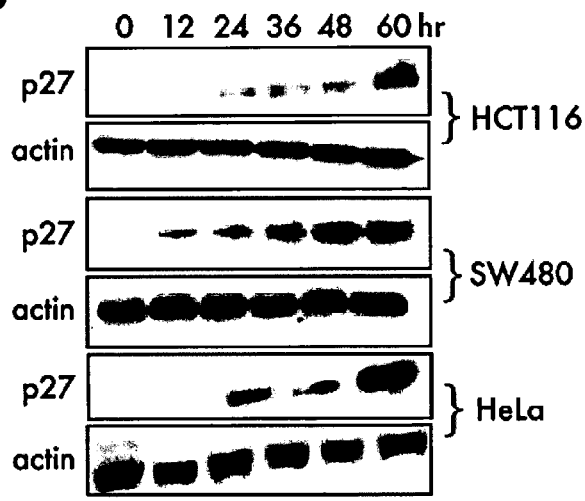

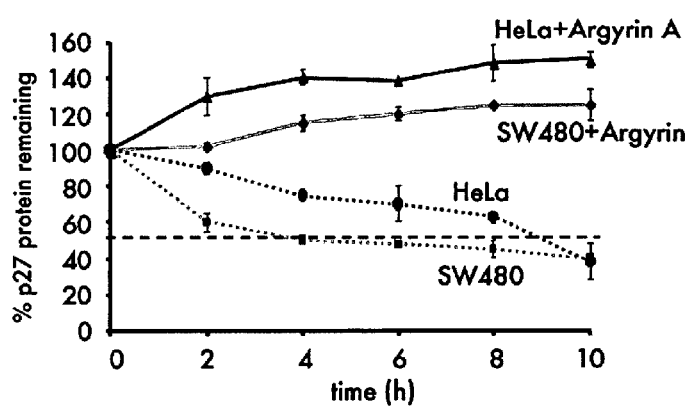

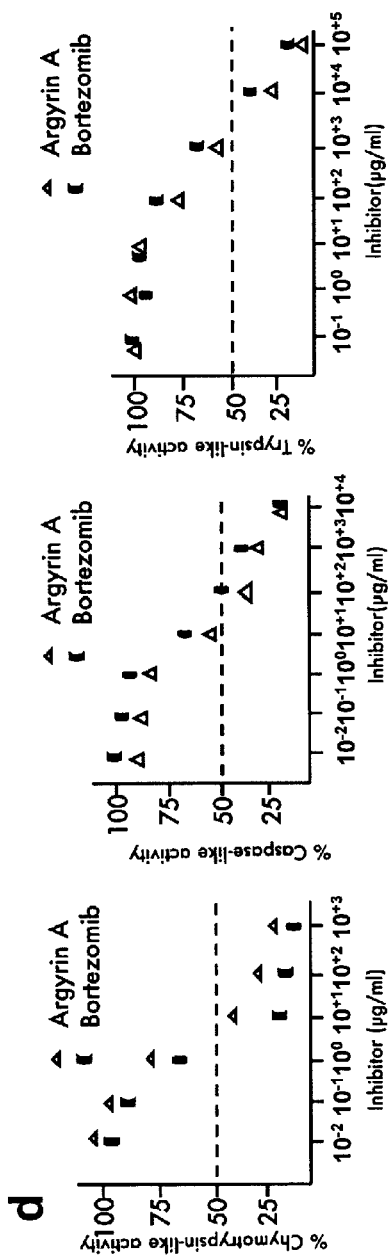

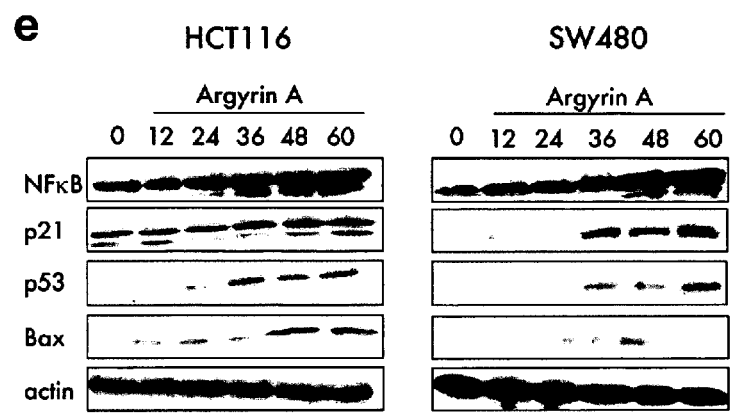

METHOD FOR PRODUCING INTERMEDIATES FOR THE PRODUCTION OF NOVEL MACROCYCLES THAT ARE INHIBITORS OF THE PROTEASOMIC DEGRADATION OF P27, SUCH AS ARGYRIN AND DERIVATIVES THEREOF, AND USES OF SAID MACROCYCLES

CROSS REFERENCE TO A RELATED APPLICATION

This application is a National Stage Application of International Application Number PCT/EP 2009/004526, filed Jun. 23, 2009; which claims priority to European Application No. 08011346.7, filed Jun. 23, 2008; which are incorporated herein by reference in their entirety.

The present invention relates to the use of particular macrocycles that are inhibitors of the proteasomic degradation of p27, in particular argyrin and derivatives thereof, for a treatment in a variety of conditions, such as the induction of immunotolerance, autoimmune diseases, bacterial infections, and proliferative diseases, such as cancers.

Reduction in the cellular levels of the cyclin kinase inhibitor p27$^{kip1}$ is frequently found in many human cancers and correlate directly with patient prognosis (Philipp-Staheli, J., Payne, S. R. and Kemp, C.J. p27(Kip1): regulation and function of a haplo-insufficient tumour suppressor and its misregulation in cancer. *Exp Cell Res* 264, 148-68 (2001)). Specifically ubiquitin dependent proteasomal turnover has been shown to cause reduced p27 expression in many human cancers (Loda, M. et al. Increased proteasome-dependent degradation of the cyclin dependent kinase inhibitor p27 in aggressive colorectal carcinomas. *Nat Med* 3, 231-4 (1997)).

U.S. Pat. No. 6,355,774 discloses the p27 protein as well as a method for producing p27 in cultured cells. In vitro assays for discovering agents which affect the activity of p27 are also provided. Furthermore, methods of diagnosing and treating hypoproliferative disorders are provided.

WO 02/055665 in Example 8 thereof describes assays that have been used to identify the interaction of Skp2 and p27 in vitro. The assays are described as useful in order to test for compounds that inhibit cell proliferation. The assays can be carried out in the presence or absence of molecules, compounds, peptides, and said molecules identified by the assays are described potentially useful drugs as therapeutic agents against cancer and proliferative disorders. No specific molecules as identified are described.

GB 2,367,553 discloses pharmaceutically active macrocycles ("argyrines") and respective pharmaceutical preparations for the treatment of autoimmune diseases, the induction of immunotolerance or the treatment of bacterial infections.

Sasse F et al. (in Sasse F, Steinmetz H, Schupp T, Petersen F, Memmert K, Hofmann H, Heusser C, Brinkmann V, von Matt P, Hofle G, Reichenbach H. Argyrins, immunosuppressive cyclic peptides from myxobacteria. I. Production, isolation, physico-chemical and biological properties. J Antibiot (Tokyo). 2002 June; 55(6):543-51.) describe the production of a group of cyclic peptides called argyrins, as well as some of their biological properties. Vollbrecht et al. (in Vollbrecht L, Steinmetz H, Hofle G, Oberer, L, Rihs G, Bovermann G, and von Matt P. Argyrins, immunosuppressive cyclic peptides from myxobacteria. II. Structure elucidation and stereochemistry. J Antibiot (Tokyo). 2002 August; 55(8):715-721.) describe the structure of said cyclic peptides.

Similarly, Ley et al. (in Ley S V, Priour A, Heusser C. Total synthesis of the cyclic heptapeptide Argyrin B: a new potent inhibitor of T-cell independent antibody formation. Org Lett. 2002 Mar. 7; 4(5):711-4.) describe the synthesis of argyrin B and its function as inhibitor of antibody formation.

EP 07004185.0 describes the use of the macrocycles of GB 2,367,553 for the production of a medicament for the treatment of cancer in a subject.

Argyrines and related macrocycles are therefore interesting candidates for the further development of medicaments for a treatment in a variety of conditions, such as the induction of immunotolerance, autoimmune diseases, bacterial infections, and proliferative diseases, such as cancers.

Nevertheless, the full exploitation of the pharmaceutical potential of argyrines and their related derivatives is difficult because of their relatively complex chemical structure, which requires laborious efforts to isolate sufficient amounts of the compounds (e.g. from microorganisms), and limits the number of effective compounds of this family that are readily available for studies and treatment.

It is therefore an object of the present invention to provide improved methods for the production of compounds of the family of argyrins, and respective intermediates. It is a further object of the present invention to further provide new members of the family of argyrines that can be used as therapeutic agents for a treatment in a variety of conditions, such as the induction of immunotolerance, autoimmune diseases, bacterial infections, and proliferative diseases, such as cancers.

According to a first aspect of the present invention, the above object is solved by a method for producing a macrocycle compound according to the following general formula (I)

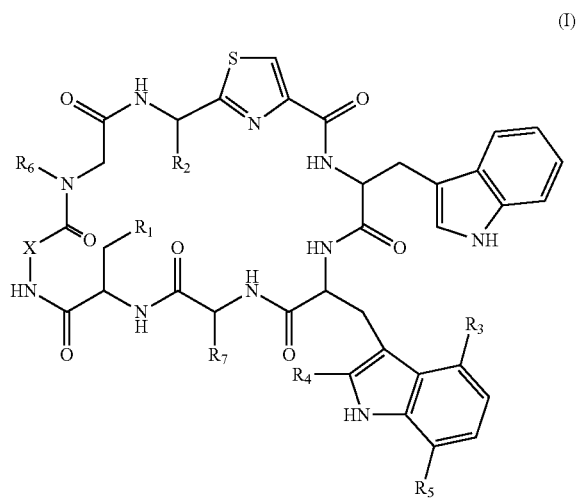

wherein
$R^1$ and $R^2$ independently are hydrogen, $C_1$-$C_4$ alkyl which is unsubstituted or substituted by OH, or $C_1$-$C_4$ alkoxy;
$R^3$ is hydrogen, $C_1$-$C_4$ alkoxy, $C_1$-$C_8$ alkyl which is unsubstituted or substituted by OH or OR, wherein R is selected from hydrogen, $C_1$-$C_4$ alkyl, aryl or acetyl, or $C_1$-$C_4$ alkoxy,
$R^4$ is hydrogen, halogen, $C_1$-$C_4$ alkyl which is unsubstituted or substituted by OH, or $C_1$-$C_4$ alkoxy;
$R^5$ is hydrogen or halogen; or C1-$C_8$ alkyl which is unsubstituted or substituted by OH or OR, $R^6$ is hydrogen or $C_1$-$C_4$ alkyl;

$R^7$ is hydrogen or $C_1$-$C_4$ alkyl which is unsubstituted or substituted by OH, or $C_1$-$C_4$ alkoxy; and X is C=$CH_2$ or $CHR^8$ wherein $R^8$ is $C_1$-$C_4$ alkyl which is unsubstituted or substituted by —S—$C_1$-$C_4$ alkyl, and stereoisomers and pharmaceutically acceptable salts thereof, wherein said synthesis comprises a synthesis starting from a thiazol-element having the general formula (II)

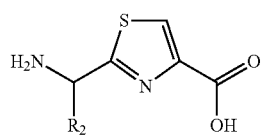

(II)

wherein and $R^2$ is independently selected from hydrogen, $C_1$-$C_4$ alkyl which is unsubstituted or substituted by OH, or $C_1$-$C_4$ alkoxy.

Preferred is a method as above, wherein if $R^1$ is not hydrogen, X must be $CH_2$.

Starting the synthesis using the thiazole-element as described herein allows for a quicker and cheaper way of synthesizing a macrocycle compound according to the general formula (I), without the inclusion of laborious steps and particularly expensive intermediates. More importantly, the use of a thiazole-derivative with protected OH-group (for $R^2$) allows for the synthesis of derivatives, and particularly new derivatives, that are derived from (e.g.) argyrin-F, which exhibit a better activity than argyrin F.

According to a second aspect of the present invention, the above object is solved by a method for producing a macrocycle compound according to the following general formula (I)

formula I

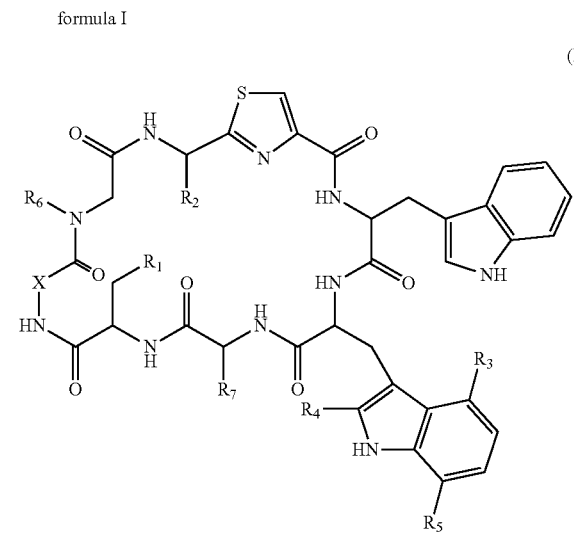

(I)

wherein $R^1$ and $R^2$ independently are hydrogen, $C_1$-$C_4$ alkyl which is unsubstituted or substituted by OH, or $C_1$-$C_4$ alkoxy;

$R^3$ is hydrogen, $C_1$-$C_4$ alkoxy, $C_1$-$C_8$ alkyl which is unsubstituted or substituted by OH or OR, wherein R is selected from hydrogen, $C_1$-$C_4$ alkyl, aryl or acetyl, or $C_1$-$C_4$ alkoxy, $R^4$ is hydrogen, halogen, $C_1$-$C_4$ alkyl which is unsubstituted or substituted by OH, or $C_1$-$C_4$ alkoxy;

$R^5$ is hydrogen or halogen;

$R^6$ is hydrogen or $C_1$-$C_4$ alkyl;

$R^7$ is hydrogen or $C_1$-$C_4$ alkyl which is unsubstituted or substituted by OH, or $C_1$-$C_4$ alkoxy; and X is C=$CH_2$ or $CHR^7$ wherein $R^7$ is $C_1$-$C_4$ alkyl which is unsubstituted or substituted by —S—$C_1$-$C_4$ alkyl, and stereoisomers and pharmaceutically acceptable salts thereof, comprising the synthesis of a tripeptide of the general formula (III)

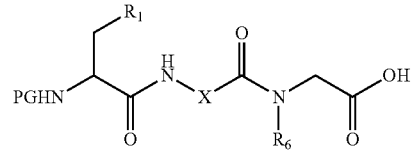

(III)

wherein

PG is a protecting group, such as Boc, Fmoc, Cbz, $R^1$ is hydrogen, $C_1$-$C_4$ alkyl which is unsubstituted or substituted by OH, or $C_1$-$C_4$ alkoxy;

$R^6$ is hydrogen or $C_1$-$C_4$ alkyl, and

X is C=$CH_2$ or $CHR^7$ wherein $R^7$ is $C_1$-$C_4$ alkyl which is unsubstituted or substituted by —S—$C_1$-$C_4$ alkyl, and stereoisomers and pharmaceutically acceptable salts thereof, which is subsequently fused with a compound according to the general formula (IV)

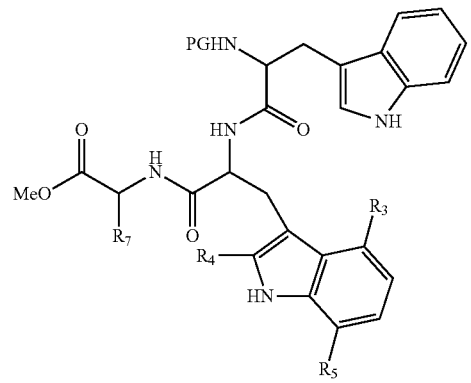

(IV)

wherein $R^3$ is hydrogen, $C_1$-$C_4$ alkoxy, $C_1$-$C_8$ alkyl which is unsubstituted or substituted by OH or OR, wherein R is selected from hydrogen, $C_1$-$C_4$ alkyl, aryl or acetyl, or $C_1$-$C_4$ alkoxy, $R^4$ is hydrogen, halogen, $C_1$-$C_4$ alkyl which is unsubstituted or substituted by OH, or $C_1$-$C_4$ alkoxy;

$R^5$ is hydrogen or halogen;

$R^7$ is hydrogen or $C_1$-$C_4$ alkyl which is unsubstituted or substituted by OH, or $C_1$-$C_4$ alkoxy;

and stereoisomers and pharmaceutically acceptable salts thereof.

Preferably, if $R^1$ is not hydrogen, X is $CH_2$.

A particular problem of the synthesis of argyrin as known is the use of a selenium-containing amino acid. In addition to the use of selenium, this route requires a final oxidation and elimination in order to establish the exo-methylene group in the argyrin. In the method according to the present invention, the double-bond is established early in the synthesis. After coupling of the amino acids serine and alanin, the double-bond can be generated through treatment with CuCl and EDC. The following peptide coupling produces the tripeptide according to formula (III). Subsequently, using the fragment according to formula (IV), the overall fusion into the macrocycle compound of the invention, such as argyrin, can be performed.

Preferred is a method for producing a macrocycle compound according to the present invention, wherein no selenium-containing amino acids are used for the synthesis.

Further preferred is a method for producing a macrocycle compound according to the present invention, wherein said macrocycle compound is selected from an argyrin, such as argyrin A-F, B/F, and Ala alpha and Ala beta, and isolated stereoisomers thereof.

Another aspect of the present invention then relates to a macrocycle compound as produced according to the present invention, which is preferably selected from the group of argyrins.

Yet another aspect of the present invention then relates to a method for producing a macrocycle compound according to the present invention which comprises the use of, optionally protected, 4-methoxy-L-tryptophane, wherein said optionally protected 4-methoxy-L-tryptophane is produced through a stereoselective catalytic hydrogenation route, comprising the steps according to the following scheme

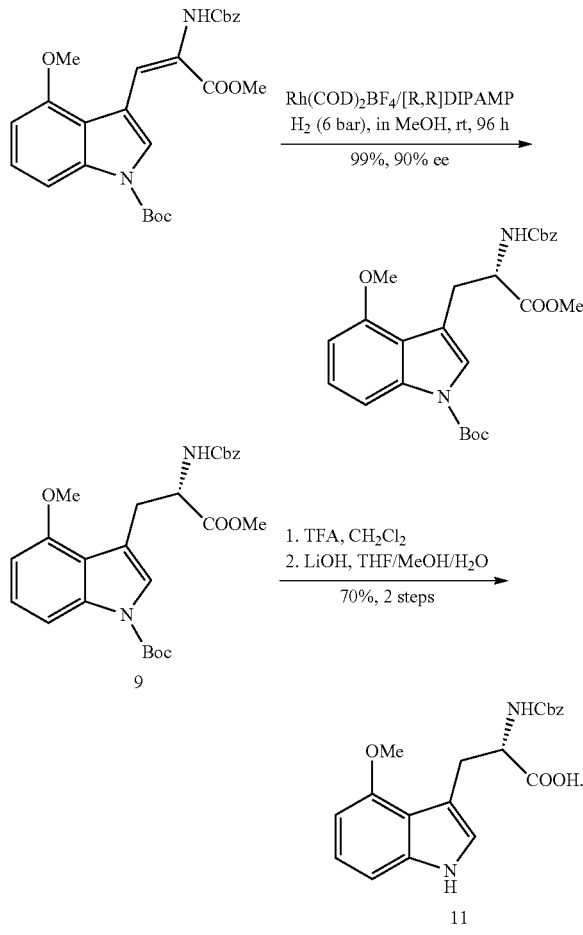

So far, the 4-methoxy-L-tryptophane could only be produced through an enzymatic resolution (Ley, S. V.; Priour, A. *Eur. J. Org. Chem.* 2002, 3995-4004; Ley, S. V.; Priour, A.; Heusser, C. *Org. Lett.* 2002, 4, 711-714). The yields that can be obtained in principal can never exceed 50%. In practice, only yields of as low as between 10 and 40% were reached.

It is furthermore a particular feature and advantage of the present invention, that the combination of the protective groups as disclosed herein, and a final acidic deprotection produces argyrin, and in particular argyrin F. It is not trivial that the t-butyl (tBu)-protective group as required for argyrin, and in particular argyrin F, can be deprotected at the end, without that compromising the double bond.

The present invention also encompasses the improved method of producing the amino acid 4-methoxy-L-tryptophane without enzymatic resolution, and uses of the product for the synthesis of macrocycles, such as argyrins.

Preferred is a method for producing a macrocycle compound according to the present invention or 4-methoxy-L-tryptophane as above, wherein the yield of the synthesis is found at more than 90%.

Further preferred is a method for producing a macrocycle compound according to the present invention or 4-methoxy-L-tryptophane as above, wherein the synthesis is performed without the uses of enzymes.

Another aspect of the present invention thus relates to 4-methoxy-L-tryptophane as produced according to the present invention, which is preferably selected from the group of argyrins.

According to another aspect of the present invention, the above object is solved by a macrocycle compound according to the following general formula (I)

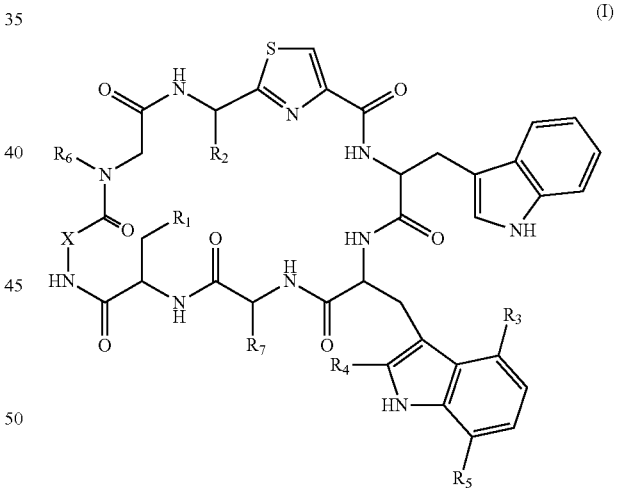

wherein
$R^1$ and $R^2$ independently are hydrogen, $C_1$-$C_4$ alkyl which is unsubstituted or substituted by OH, or $C_1$-$C_4$ alkoxy;
$R^3$ is hydrogen, $C_1$-$C_4$ alkoxy, $C_1$-$C_8$ alkyl which is unsubstituted or substituted by OH or OR, wherein R is selected from hydrogen, $C_1$-$C_4$ alkyl, aryl or acetyl, or $C_1$-$C_4$ alkoxy,
$R^4$ is hydrogen, halogen, $C_1$-$C_4$ alkyl which is unsubstituted or substituted by OH, or $C_1$-$C_4$ alkoxy;
$R^5$ is hydrogen or halogen;
$R^6$ is hydrogen or $C_1$-$C_4$ alkyl;
$R^7$ is different from a proton, and
X is C=$CH_2$ or $CHR^7$ wherein $R^7$ is $C_1$-$C_4$ alkyl which is unsubstituted or substituted by —S—$C_1$-$C_4$ alkyl.

Preferably, $R^7$ is hydrogen or $C_1$-$C_4$ alkyl which is unsubstituted or substituted by OH, or $C_1$-$C_4$ alkoxy; and X is C=$CH_2$ or $CHR^7$ wherein $R^7$ is $C_1$-$C_4$ alkyl which is unsubstituted or substituted by —S—$C_1$-$C_4$ alkyl.

Preferably, if $R^1$ is not hydrogen, X must be $CH_2$,

Preferred is a macrocycle compound according to the present invention that is selected from the following formula (V)

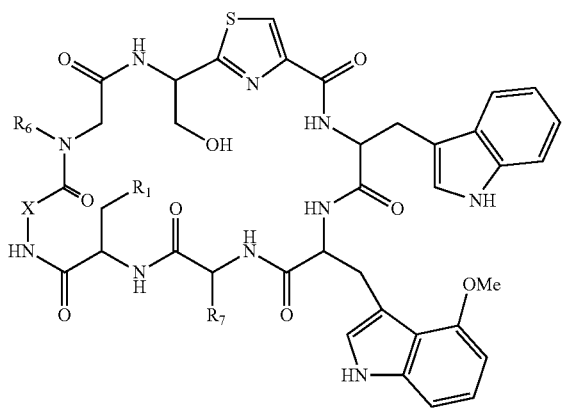

(V)

wherein $R^1$ is hydrogen, $C_1$-$C_4$ alkyl which is unsubstituted or substituted by OH, or $C_1$-$C_4$ alkoxy;

$R^6$ is hydrogen or $C_1$-$C_4$ alkyl;

$R^7$ is hydrogen or $C_1$-$C_4$ alkyl which is unsubstituted or substituted by OH, or $C_1$-$C_4$ alkoxy; and X is C=$CH_2$ or $CHR^7$ wherein $R^7$ is $C_1$-$C_4$ alkyl which is unsubstituted or substituted by —S—$C_1$-$C_4$ alkyl. Preferably, if R' is not hydrogen, X must be $CH_2$, The results of the inventors have shown that argyrin Ala beta has a stronger inhibiting effect on the proteasome than argyrin F, and of all three proteasome-subunits. Without wanting to be bound by theory, the configuration thus appears to be important. Argyrin Ala alpha was found as slightly less active. The synthesis would be similar to the one of argyrin F. Nevertheless, the concept of including alanin at this position is not at all trivial, since this results in a conformational change that could not be foreseen by the person of skill. On the other hand, this change leads to the markedly improved activity in the proteasome-assay (see Examples, below). This inclusion of alanin is therefore particularly preferred.

Particularly preferred is a macrocycle compound according to the present invention that is selected from the following formulae

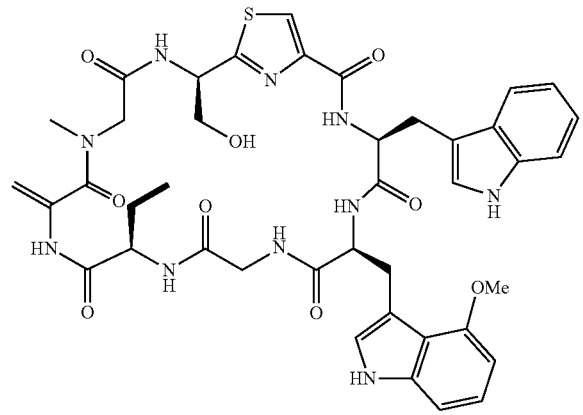

Argyrin B/F

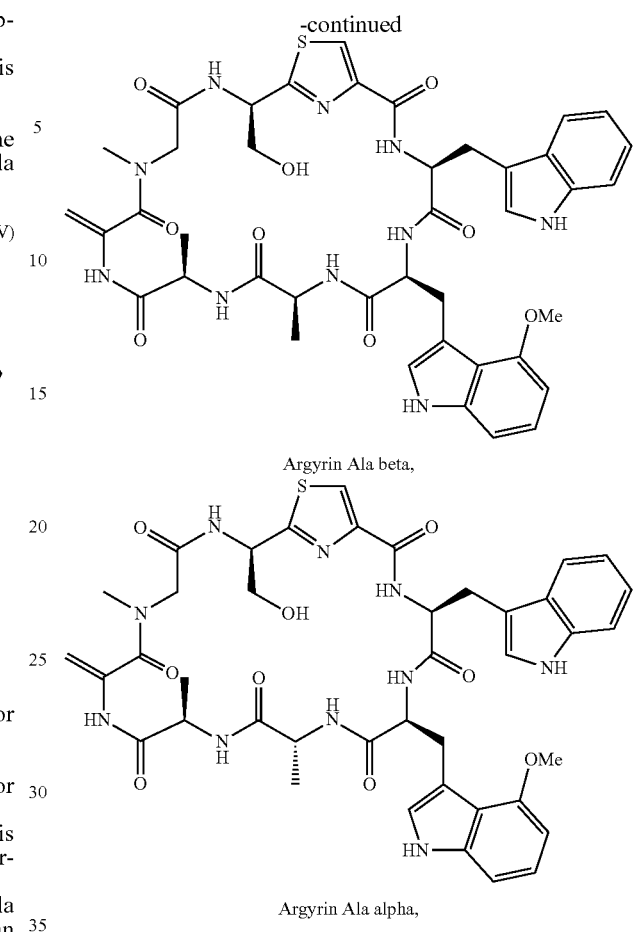

Argyrin Ala beta,

Argyrin Ala alpha, and pharmaceutically acceptable salts thereof.

Further preferred is a macrocycle compound according to the present invention that is further chemically modified. More preferred is a method according to the present invention, wherein the method further comprises a chemical modification of the compound according to the present invention. In this case, the compound will function as a so-called "lead-structure" which is further subjected to chemical modifications which are then screened for their effectiveness to increase the amount and/or biological activity of p27 in one or more subsequent screening methods as known.

Modification can be effected by a variety of methods known in the art, which include without limitation the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, isopropyl, n-butyl, isobutyl, tert-butyl, n-pentyl or iso-pentyl groups, lower alkenyl groups, preferably having two to five carbon atoms, lower alkynyl groups, preferably having two to five carbon atoms or through the introduction of, for example, a group selected from the group consisting of $NH_2$, $NO_2$, OH, SH, NH, CN, aryl, heteroaryl, COH or COOH group. Furthermore, additional peptide groups could be added to the molecule, such as single amino acids, dipeptides, tripeptides, and so on.

Another aspect of the present invention then relates to a macrocycle compound according to the present invention for use in the treatment of conditions and diseases in a subject. Preferably, said subject is a mammal, in particular a human.

Yet another aspect of the present invention is directed to a method for producing a pharmaceutical composition, comprising formulating the compound according to the present invention with pharmaceutically acceptable carriers and/or excipients. Carriers, excipients and strategies to formulate a pharmaceutical composition, for example to be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form are well known to the person of skill and described in the respective literature.

Administration of an agent, e.g., a compound can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

Yet another aspect of the present invention is then directed to a pharmaceutical composition that is produced according to the method as above.

Another aspect of the present invention relates to a method of treating a disease or condition in a subject, comprising administering an effective amount of the pharmaceutical preparation according to present invention to a subject in need of said treatment. Preferably, said disease or condition is selected from the induction of immunotolerance, autoimmune diseases, bacterial infections, and proliferative diseases, such as psoriasis or cancers, such as breast cancer, hepatocellular carcinoma, myeloma, cervix carcinoma, lung carcinoma, and colon cancer. Preferably, said patient is a human being. Treating is meant to include, e.g., preventing, treating, reducing the symptoms of, or curing the disease or condition.

The invention also includes a method for treating a subject at risk for a disease as above, wherein a therapeutically effective amount of a compound as above is provided. Being at risk for the disease can result from, e.g., a family history of the disease, a genotype which predisposes to the disease, or phenotypic symptoms which predispose to the disease.

Another aspect of the present invention then relates to a method for treating a subject according to the present invention, wherein the medicament further comprises additional pharmaceutically active anti-tumor ingredients, such as paclitaxel, bortezomib or antibacterial agents, such as an antibiotic.

Preliminary mouse experiments as performed by the present inventors show that argyrin is active already at a concentration of 0.03 mg/kg body weight. Another aspect of the present invention thus relates to a use according to the present invention, wherein the compound according to the present invention is administered at a dose of 0.01 mg to 200 mg/kg, preferably at a dose of 0.01 mg to 100 mg/kg, most preferably at a dose of 0.02 mg to 10 mg/kg, optimally given per day. Another example is 0.15 mg of the compound per kilogram bodyweight injected intraperitoneally every three days.

In certain embodiments of the invention, the administration can be designed so as to result in sequential exposures to the compound over some time period, e.g., hours, days, weeks, months or years. This can be accomplished by repeated administrations of the compound, e.g., by one of the methods described above, or alternatively, by a controlled release delivery system in which the compound is delivered to the subject over a prolonged period without repeated administrations. By a controlled release delivery system is meant that total release of the compound does not occur immediately upon administration, but rather is delayed for some time. Release can occur in bursts or it can occur gradually and continuously. Administration of such a system can be, e.g., by long acting oral dosage forms, bolus injections, transdermal patches or subcutaneous implants. Examples of systems in which release occurs in bursts include, e.g., systems in which the compound is entrapped in liposomes which are encapsulated in a polymer matrix, the liposomes being sensitive to a specific stimulus, e.g., temperature, pH, light, magnetic field, or a degrading enzyme, and systems in which the compound is encapsulated by an ionically-coated microcapsule with a microcapsule core-degrading enzyme. Examples of systems in which release of the compound is gradual and continuous include, e.g., erosional systems in which the compound is contained in a form within a matrix, and diffusional systems in which the compound permeates at a controlled rate, e.g., through a polymer. Such sustained release systems can be, e.g., in the form of pellets or capsules.

The compound can be administered prior to or subsequent to the appearance of disease symptoms. In certain embodiments, the compound is administered to patients with familial histories of the disease, or who have phenotypes that may indicate a predisposition to the disease, for example breast cancer, or who have been diagnosed as having a genotype which predisposes the patient to the disease, or who have other risk factors.

The compound according to the invention is administered to the subject in a therapeutically effective amount. By therapeutically effective amount is meant that amount which is capable of at least partially preventing or reversing the disease or condition. A therapeutically effective amount can be determined on an individual basis and will be based, at least in part, on consideration of the species of subject, the subject's size, the subject's age, the efficacy of the particular compound used, the longevity of the particular compound used, the type of delivery system used, the time of administration relative to the onset of disease symptoms, and whether a single, multiple, or controlled release dose regimen is employed. A therapeutically effective amount can be determined by one of ordinary skill in the art employing such factors and using no more than routine experimentation.

In certain preferred embodiments, the concentration of the compound according to the present invention is at a dose of about 0.1 to about 1000 mg/kg body weight/day, more preferably at about 0.01 mg to 200 mg/kg, preferably at a dose of about 0.01 mg to 100 mg/kg, most preferably at a dose of 0.02 mg to 10 mg/kg. Preferably, the dosage form is such that it does not substantially deleteriously affect the subject.

Compounds of the invention may also be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form.

Another aspect of the present invention is the use of a compound according to the present invention for the treatment of a disease or condition selected from the induction of immunotolerance, autoimmune diseases, bacterial infections, and proliferative diseases, such as psoriasis or cancers, such as breast cancer, hepatocellular carcinoma, myeloma, cervix carcinoma, lung carcinoma, and colon cancer. Yet another aspect of the present invention is the use of a compound according to the present invention for the production of a medicament for the treatment of a disease or condition selected from the induction of immunotolerance, autoimmune diseases, bacterial infections, and proliferative diseases, such as psoriasis or cancers, such as breast cancer, hepatocellular carcinoma, myeloma, cervix carcinoma, lung carcinoma, and colon cancer.

The following figures, sequences, and examples merely serve to illustrate the invention and should not be construed to restrict the scope of the invention to the particular embodiments of the invention described in the examples. For the purposes of the present invention, all references as cited herein are hereby incorporated herein by reference in their entireties.

LEGEND FOR FIGURE

FIG. 1 shows that argyrin A induces p27 stabilization through inhibition of the 20S proteasome. a) The indicated cell lines were treated with Argyrin A and the G1 and sub-G1 fractions were determined by flow cytometric analysis of propidium iodide stained cells. IC50 values were determined by MTT cell proliferation assays using different concentrations of Argyrin A. The IC50 value was calculated as the half-maximal concentration at which Argyrin A exerted an effect. b) SW480, HCT116 and HeLa cells were treated with Argyrin A after which cells were lysed at the indicated timepoints to determine the expression levels of p27kip1 by western blotting. c) SW480 and HeLa cells were treated with Argyrin A or left untreated for 12 hours after which time cycloheximide was added at a concentration of 25 µg/mL. The expression levels of p27kip1 were determined at the indicated timepoints by western blotting and normalized against actin expression which was used as an internal control. The graphs shows a quantification of three independent experiments. d) Purified human erythrocyte derived 20S proteasome was incubated with the indicated amounts of Argyrin A or bortezomib and the activity of the caspase-, chymotrypsin- and trypsin-like proteasome activities were measured using fluorogenic peptide substrates specific for the different catalytic activities. e) SW480 and HCT116 cell lines were incubated with Argyrin A. At the indicated timepoints cells were lysed and the expression levels of p53, p21, Bax, NfkB and actin were analyzed by western blotting.

EXAMPLES

It should be understood that the following syntheses can be readily modified by the person of skill in order to synthesize other derivatives of the present invention based on the strategies as provided.

1. Synthesis of 4-Methoxy-L-tryptophane (10)

In order to avoid the fundamental problems in synthesizing (10) the stereoselective catalytic hydrogenation was established as a new, efficient and economic synthesis method. Substrate 8, which can be synthesized in very good yield, served as a starting material.

Scheme 2 Synthesis of fragment 8.

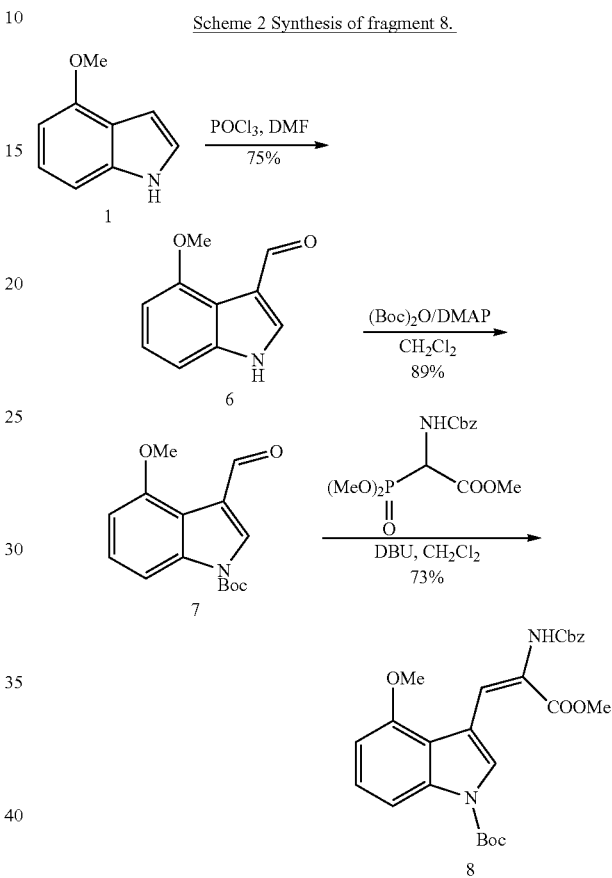

A chiral biphosphine rhodium catalyst as developed by Knowles et al. served as catalyst. R,R-DIPAMP is used as the ligand, which could be converted into the catalyst as required in accordance with a simple recipe with [Rh(COD)Cl]$_2$ and sodium tetrafluoroborate. (Refs 2, 3, and 4)

The hydrogenation was performed in an autoclave at 6 bar. The enantioselectivity, as well as the absolute configuration was determined with the Mosher-method following Cbz-deprotection.

Scheme 3 Hydrogenation of fragment 8.

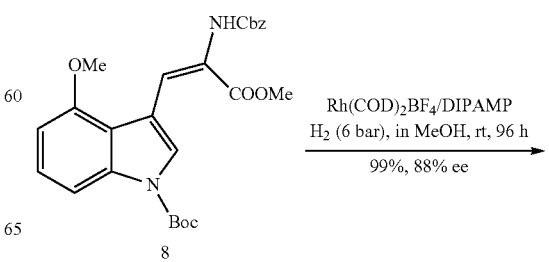

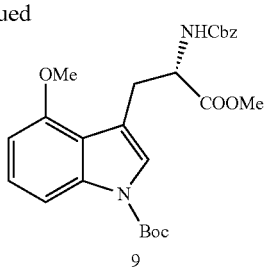

9

Compound 9 could be converted in a two-step reaction sequence using Boc-deprotection with trifluoroacetic acid and hydrolysis of the methyl ester with 0.5 N aqueous solution of LiOH in tetrahydrofurane/water/methanol in very good yields into the desired cbz-protected 4-methoxy-L-tryptophan 10.

Scheme 4 Boc-deprotection followed by hydrolysis of the ester leads to Cbz protected 4-methoxy tryptophane 10.

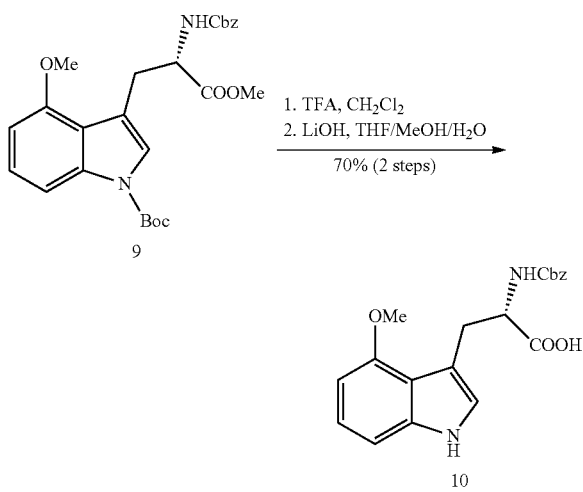

Using this new reaction sequence, 4-methoxy-L-tryptophan (10) can be obtained in the decisive last step with 99% yield and 90% ee. In addition, the enantiomeric excess (ee) can be improved to >95% by a subsequent recrystallization.

Synthesis of Aldehyde 6

Phosphorous oxychloride (0.47 mL, 5.10 mmol) was added dropwise to dry dimethylformamide (3 mL) at 0° C. At this temperature, the methoxyindol 6 (500 mg, 3.40 mmol) in dry dimethylformamide (2 mL) was slowly added, whereby a bright-yellow precipitate forms. The reaction mixture was warmed to 45° C., and stirred for two hours. The reaction was poured onto ice water (8 mL), extracted twice with diethyl ether and the ethereal extracts discarded. The aqueous layer was then treated with aqueous sodium hydroxide until the solution was basic and extracted with diethyl ether. The organic extracts were washed with brine, dried (MgSO$_4$) and concentrated under reduced pressure to give crude product as a pale-yellow crystalline solid (440 mg, 2.51 mmol, 74%).

$^1$H-NMR (400 MHz, CDCl$_3$): δ=10.50 (s, 1 H), 9.06 (br. s, 1 H), 7.93 (d, J=3.1 hz, 1 H), 7.22 (t, J=8.0 Hz, 1 H), 7.09 (d, J=8.2 Hz, 1 H), 6.73 (d, J=7.9 Hz, 1 H), 4.01 (s, 3 H).

$^{13}$C-NMR (100 MHz, CDCl$_3$): δ=188.6, 154.6, 137.6, 128.1, 124.3, 119.6, 116.1, 105.1, 102.5, 55.4.

HRMS (ESI) calculated for C$_{10}$H$_{10}$NO$_2$ ([M]$^+$): 176.0712, found: 176.0708.

Synthesis of Aldehyde 7

Methoxyindol-3-carbaldehyde 6 (440 mg, 2.51 mmol) was dissolved in dichloromethane (6 mL) and treated at room temperature with DMAP (31 mg, 0.25 mmol) and di-tert-butyl dicarbonate (660 mg, 3.02 mmol). After stirring for one hour, 1 N KHSO$_4$ solution (4.4 mL) was added and dichloromethane was evaporated. The aqueous layer was extracted with several portions of diethyl ether and the combined organic extracts were washed with 1 N KHSO$_4$, water, 1 N NaHCO$_3$, and brine. The organic layer was dried (MgSO$_4$) and concentrated under reduced pressure to give aldehyde 7 (605 mg, 2.20 mmol, 87%) as a white solid.

$^1$H-NMR (400 MHz, CDCl$_3$): δ=10.55 (s, 1 H), 8.23 (s, 1 H), 7.84 (d, J=8.5 Hz, 1 H), 7.32 (t, J=8.2 Hz, 1 H), 6.81 (d, J=7.9 Hz, 1 H), 4.00 (s, 3 H), 1.67 (s, 9 H).

$^{13}$C-NMR (100 MHz, CDCl$_3$): δ=189.1, 154.1, 149.0, 137.1, 128.7, 126.1, 121.4, 117.2, 108.6, 104.5, 85.4, 55.5, 28.0.

HRMS (EI) calculated for C$_{15}$H$_{17}$NO$_4$ ([M]$^+$): 275.1158, found: 275.1159.

Synthesis of Dehydro Amino Acid 8

To a solution of phosphonate 9 (217 mg, 0.65 mmol) in dichloromethane (0.6 mL) was added DBU (0.09 mL, 0.60 mmol). After 10 minutes stirring, aldehyde 8 (150 mg, 0.55 mmol) in dichloromethane (0.6 mL) was added slowly. After the reaction mixture was stirred for 5 hours, the solvent was evaporated under reduced pressure. The residue was dissolved in ethyl acetate (18 mL), then the organic solution was washed with 1 N HCl (2×5 mL) and brine, dried (MgSO$_4$), and concentrated. The crude product was purified by flash chromatography (ethyl acetate/hexanes: 1/5) to give a yellow solid (191 mg, 0.40 mmol, 73%).

$^1$H-NMR (400 MHz, CDCl$_3$): δ=8.32 (s, 1 H), 7.93 (s, 1 H), 7.77 (d, J=8.2 Hz, 1 H), 7.40-7.30 (m, 5 H), 7.28-7.24 (m, 1 H), 6.73 (d, J=8.2 Hz, 1 H), 6.14 (br. s, 1 H), 5.20 (s, 2 H), 3.96 (s, 3 H), 3.83 (s, 3 H), 1.63 (s, 9 H).

$^{13}$C-NMR (100 MHz, CDCl$_3$): δ=154.7, 136.5, 136.2, 128.7, 128.3, 128.2, 127.9, 126.5, 126.0, 114.2, 108.4, 104.4, 84.7, 67.6, 55.6, 52.6, 28.2.

HRMS (ESI) calculated for C$_{26}$H$_{28}$N$_2$O$_7$Na ($_{[M+Na]}^+$): 503.1794, found: 503.1760.

Synthesis of the rhodium catalyst cyclooctadien-1,5-[(R,R)-DIPAMP]rhodium tetra-fluoroborate Bis(cyclooctadiene-1,5)dichlorodirhodium [Rh(COD)Cl]$_2$ (97 mg, 0.2 mmol) was added to a solution of (R,R)-DIPAMP (180 mg, 0.39 mmol) in methanol (1.5 mL) and water (0.5 mL). The slurry became orange and after stirring for 1 hour gave a red-orange solution. The complex was precipitated by adding slowly a solution of sodium tetra-fluoroborate (65 mg, 0.6 mmol) in water (0.5 mL) over 30 minutes. After 2.5 hours stirring at room temperature the fine crystals were filtered, washed twice with small portions of water, and dried at high vacuum. There was obtained 210 mg (71%) of the catalyst cyclooctadien-1,5-[(R,R)-DIPAMP] rhodium tetrafluoroborate. The catalyst was used without further purification.

Hydrogenation of Dehydro Amino Acid 8

An autoclave was charged with catalyst cyclooctadien-1,5-[(R,R)-DIPAMP]rhodium tetra-fluoroborate (29 mg, 0.040 mmol), dehydro amino acid 8 (500 mg, 1.04 mmol) and methanol (20 mL). After three vacuum/hydrogen cycles, the autoclave was pressurized to an initial pressure of 6 bar. The reaction was allowed to proceed for 4 days. After the evaporation of the solvent, the crude product was purified by column chromatography to give tryptophane 9 (497 mg, 1.03 mmol, 99%, 90%ee) as a colorless oil.

Rf=0.17 (ethyl acetate/n-hexane 1:3).

$[\alpha]_{589}^{20}$=+3.0 (11 mg, c=1.1, CHCl$_3$)

$^1$H-NMR (400 MHz, CDCl$_3$): δ=7.78 (d, J=8.2 Hz, 1 H), 7.38-7.19 (m, 7 H), 6.66 (d, J=8.2 Hz, 1 H), 5.77 (d, J=7.5 Hz, 1 H), 5.04 (s, 2 H), 4.66 (ddd, J=8.0, 8.0, 5.1 Hz, 1 H), 3.92 (s, 3 H), 3.73 (s, 3H), 3.43-3.33 (m, 1 H), 3.19 (dd, J=14.3, 8.9 Hz, 1 H), 1.65 (s, 9 H).

$^{13}$C-NMR (100 MHz, CDCl$_3$): δ=172.8, 156.0, 153.7, 149.6, 137.2, 136.5, 128.6, 128.1, 128.0, 127.8, 125.5, 123.5, 119.7, 115.4, 108.7, 83.8, 66.8, 55.6, 55.3, 52.3, 29.3, 28.3.

HRMS (ESI) calculated for C$_{26}$H$_{31}$N$_2$O$_7$ ([M]$^+$): 483.2131, found: 483.2133.

Synthesis of Mosher-amide 11

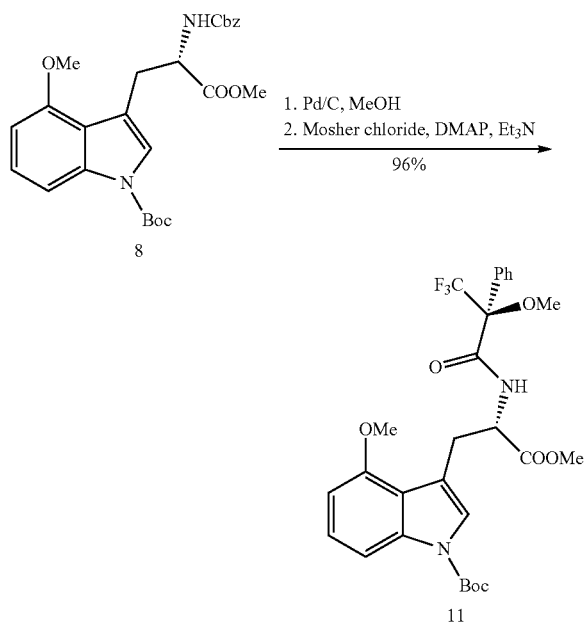

Palladium on charcoal (100 mg, 10% weight) was added to a solution of N$^\alpha$-Cbz-N$^{Ind}$-Boc-L-Trp-OMe 8 (20 mg, 0.04 mmol) in methanol (1 ml). The reaction mixture was purged with hydrogen three times and stirred for 12 hours at room temperature. The suspension was fil-tered through a plug of Celite®, washed with methanol (2×3 mL) and concentrated. The amine was used directly in the next step.

To a solution of the amine (5 mg, 14 μmol) in dichloromethane (1 mL) was added at room temperature successively triethylamine (16 μL, 115 μmol), DMAP (3.2 mg, 26 μmol), (S)-Mosher chloride (11 μL, 58 μmol). The mixture was stirred at room temperature for 3 hours and quenched with ethyl acetate (10 mL). The mixture was washed successively with saturated aqueous NaHSO$_4$ (5 mL), 1 N NaOH (5 mL) and saturated aqueous NaHCO$_3$ (2×5 mL). The organic phase was dried over MgSO$_4$, filtered and concentrated under reduced pressure. The crude residue was purified by flash chromatography to afford the corresponding Mosher ester 11 (8 mg, 14 μmol, 96%).

Rf=0.18 (Ethyl acetate/n-hexane 1:3);

$^1$H-NMR (400 MHz, CDCl$_3$): δ=7.83 (d, J=6.8 Hz, 1 H), 7.79 (d, 8.5 Hz, 1 H), 7.60-7.53 (m, 2 H), 7.43-7.36 (m, 3 H), 7.33 (s, 1 H), 7.25-7.21 (m, 1 H), 6.67 (d, J=7.9 Hz, 1 H), 4.78-4.70 (m, 1 H), 3.77 (s, 3 H), 3.75 (s, 3 H), 3.43-3.35 (m, 1 H), 3.28 (dd, J=14.3, 9.9 Hz, 1 H), 2.92 (d, J=1.4 Hz, 3 H), 1.66 (s, 9 H).

$^{13}$C-NMR (100 MHz, CDCl$_3$): δ=171.8, 166.9, 153.5, 149.5, 133.0, 129.7, 129.6, 128.6, 128.3, 128.2, 125.6, 125.2, 123.6, 119.6, 115.3, 108.9, 103.3, 84.0, 77.4, 55.2, 54.9, 52.4, 28.3, 28.0.

HRMS (ESI) calculated for C$_{28}$H$_{31}$N$_2$O$_7$F$_3$Na ([M+Na]$^+$): 587.1981, found: 587.1982.

Synthesis of Cbz-Protected Methoxytryptophane 10

Trifluoroacetic acid (0.5 mL) was added dropwise to a solution of methoxytryptophane 9 (95 mg, 0.20 mmol) in dichloromethane (4 mL) at 0° C. The reaction mixture was stirred for 3.5 hours at room temperature. The solution was concentrated by co-evaporation with toluene (3×5 mL) and the resulting deprotected tryptophane was used directly in the next step.

A 0.5 N aqueous solution of LiOH (0.8 mL, 0.4 mmol) was added to a solution of the deprotected tryptophane in tetrahydrofurane/methanol/water (7:1.3:4 mL) at 0° C. The reaction mixture was warmed to room temperature and stirred for 2 hours. The solution was partitioned between 0.1 N aqueous HCl (15 mL) and dichloromethane (15 mL). The aqueous layer was extracted with dichloromethane (2×15 mL) and the organic layers were combined, dried (Na$_2$SO$_4$) and concentrated. The residue was purified by column chromatography (dichloromethane with a gradient of 1 to 5% methanol) to give 51 mg of Cbz-protected methoxytryptophane 10 as a white solid (0.14 mmol, 70%, 2 steps).

Rf=0.27 (Ethyl acetate/n-hexane 3:1, with 1% acetic acid);

$[\alpha]_{589}^{20}$=−44.3 (c=0.3, MeOH)

$^1$H-NMR (400 MHz, [D6]DMSO, 60° C.): δ=10.75 (br, s, 1H), 7.41 (d, J=8 Hz, 1H), 7.24-7.34 (m, 5H), 6.9-7.2 (m, 3H), 6.44 (d, J=7 Hz, 1H), 4.95 (m, 2H), 4.30 (m, 1H), 3.83 (s, 3H), 3.35 (dd, J=14, 4 Hz, 1H), 2.95 (dd, J=14, 10 Hz, 1H).

2. Synthesis of Fmoc-Protected Amino Acids (31 and 32) for Use in Solid Phase Synthesis of Argyrins The solid phase peptide synthesis is a technique that allows for the rapid and efficient assembly of peptides through automation. The most common protecting group strategy used therein is the Fmoc-strategy for the removal of nitrogen protecting groups under basic conditions. In the present invention, the inventors describe a synthesis that allows the assembly of the pivotal amino acids (methoxy tryptophane and the thiazole containing amino acid) as their Fmoc derivatives. The particular challenge in these syntheses has been a) the base lability of the Fmoc group that required a different synthetic route and strategy in particular for the thiazole amino acid compared to published routes and b) to develop a route that prevented epimerization of the chiral centers. The latter was particularly challenging for the thiazole amino acid.

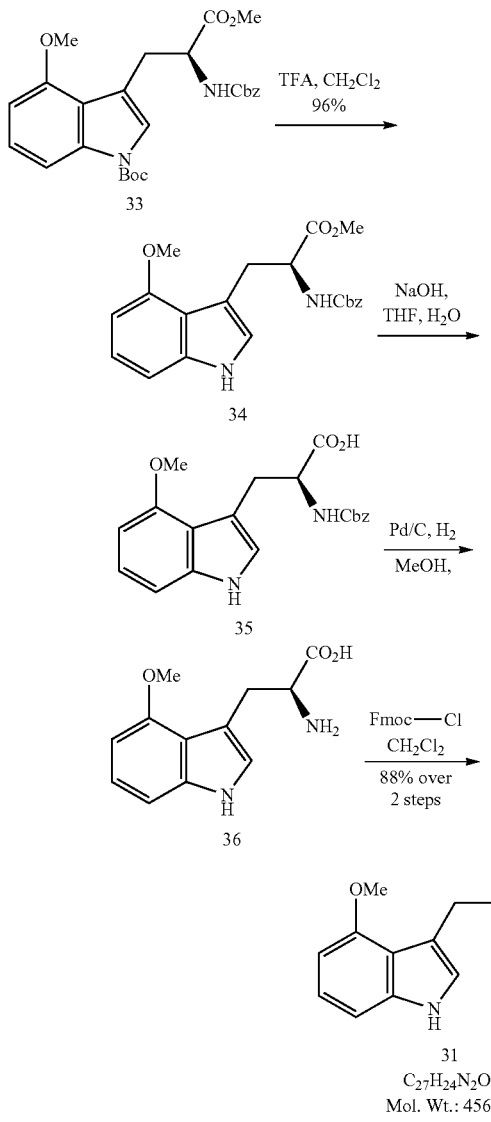

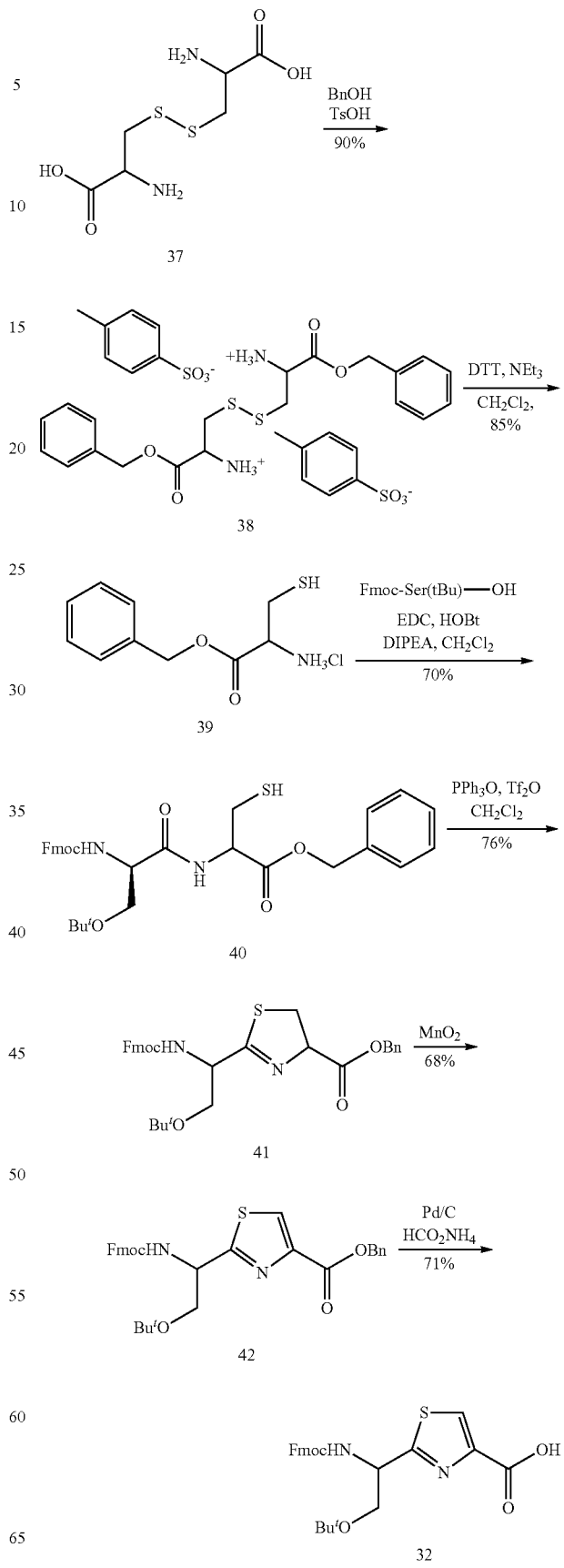

The synthesis of the tryptophane amino acid used intermediate 32 which was used in our synthesis of the Boc-protected amino acid. Removal of the Boc protecting group established compound 33 which was saponified to provide amino acid 34. After hydrogenolysis, the alpha amino moiety was protected to provide the Fmoc-protected amino acid required for solid phase synthesis.

The synthesis of the thiazole moiety containing amino acid begins with cystine (37) and treatment with benzyl alcohol and acidic conditions provides benzyl ester 38. The disulfide bond can be cleaved with DTT and the t-Butyl protected serine is coupled under standard conditions. The pivotal ring closure which can cause significant epimerization can be performed with TfO$_2$ and O=PPh$_3$ to produce thiazolin 41 in 76% yield and without detectable epimerization (ee>90%). The aromatization is achieved with MnO$_2$ and final hydrogenation provides the Fmoc-protected amino acid 32.

Syntheses of the Fmoc-Protected Fragments

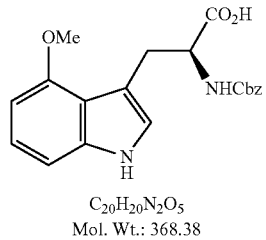

C<sub>20</sub>H<sub>20</sub>N<sub>2</sub>O<sub>5</sub>
Mol. Wt.: 368.38

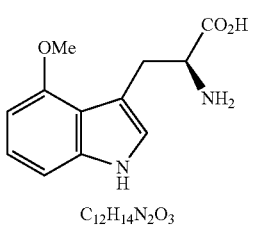

C<sub>12</sub>H<sub>14</sub>N<sub>2</sub>O<sub>3</sub>
Mol. Wt.: 234.25

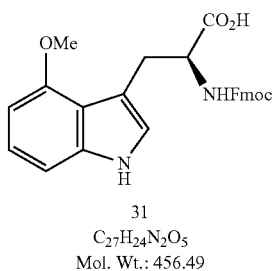

31
C<sub>27</sub>H<sub>24</sub>N<sub>2</sub>O<sub>5</sub>
Mol. Wt.: 456.49

A solution of Cbz-protected methoxytryptophan 35 (368 mg, 1 mmol) and Pd/C (10%, 50 mg) in MeOH was hydrogenated for 3 h. The mixture was filtered and evaporated. The crude acid in dioxane (5 mL) and aq. Na$_2$CO$_3$ solution (10%, 10 mL) was treated with Fmoc-Cl (259 mg, 1 mmol). The mixture was stirred for 2 h at 0° C. Then water (100 mL) was added and the aqueous layer was washed with MTBE. The aqueous layer was acidified with HCl (1M) and extracted with CH$_2$Cl$_2$. The organic phase was dried (MgSO$_4$) and the solvent removed to afford Fmoc-protected methoxytryptophan 31 (402 mg, 88%).

$[\alpha]_{589}^{20}$=−31.8 (c=0.34, MeOH).

$^1$H-NMR (400 MHz, DMSO-d$_6$): δ=12.50 (br. s, 1H), 10.81 (s, 1H), 7.87 (d, J=7.85 Hz, 2H), 7.65 (d, J=7.51 Hz, 1H), 7.61 (d, J=7.51 Hz, 1H), 7.55 (d, J=8.19 Hz, 1H), 7.42 (d, J=7.17 Hz, 1H), 7.38 (d, J=7.17 Hz, 1H), 7.31 (t, J=7.51 Hz, 1H), 7.25 (t, J=7.51 Hz, 1H), 7.02 (s, 1H), 7.00-6.90 (m, 2H), 6.45 (d, J=7.17 Hz, 1H), 4.29 (m, 1H), 4.18 (m, 3H), 3.82 (s, 3 H), 3.00 (m, 1H).

$^{13}$C-NMR (100 MHz, DMSO-d$_6$): δ=155.8, 154.0, 143.9, 143.8, 140.7, 137.8, 128.9, 128.3, 127.6, 127.5, 127.3, 127.1, 125.2, 122.5, 121.7, 121.4, 120.1, 116.9, 110.7, 109.8, 105.0, 98.8, 66.4, 55.9, 55.0, 48.6, 46.6.

HRMS (ESI): C<sub>27</sub>H<sub>25</sub>N<sub>2</sub>O<sub>5</sub> ([M]$^+$) requires 457.1763, found 457.1769.

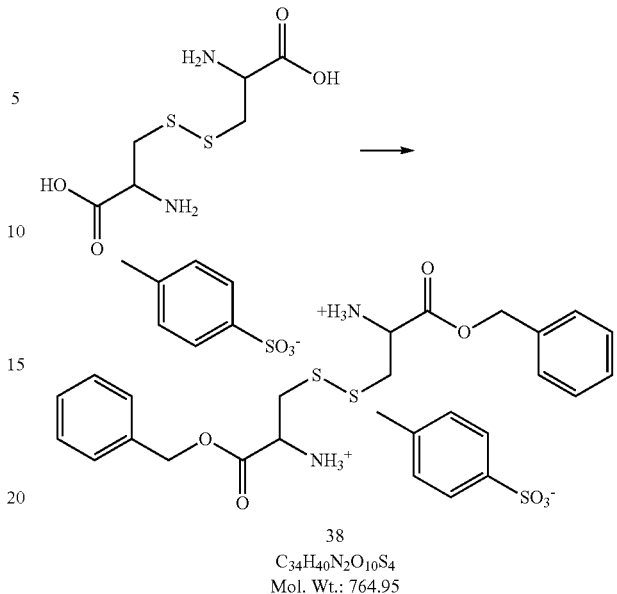

38
C<sub>34</sub>H<sub>40</sub>N<sub>2</sub>O<sub>10</sub>S<sub>4</sub>
Mol. Wt.: 764.95

Literature: *JACS* 2005, 12263 (Allylester)

A round bottomed flask equipped with a Dean Stark seperator was charged with L-cystine (20 g, 20.8 mmol), benzyl alcohol (100 mL, 249.6 mmol) and p-TsOH.H$_2$O (63.3 g, 83.2 mmol) in benzene (500 mL). The mixture was heated to reflux until the calculated amount of water was separated (3-5 h). After cooling to r.t. the precipitated product was suction-filtered, washed with ethyl acetate and dried to afford 38 (60 g, 94%).

$^1$H-NMR of 38-TsOH (400 MHz, CDCl$_3$): δ=7.40-7.30 (m, 10H), 5.15 (s, 4H), 3.85 (dd, J=7.9, 4.8 Hz, 2H), 3.13 (dd, J=13.7, 4.4 Hz, 2H), 2.92 (dd, J=13.7, 7.5 Hz, 2H), 2.09 (br. s, 4H).

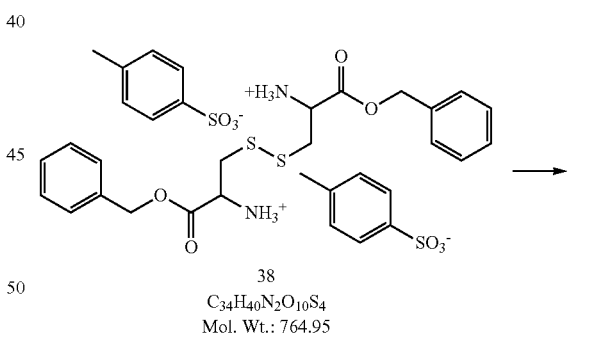

38
C<sub>34</sub>H<sub>40</sub>N<sub>2</sub>O<sub>10</sub>S<sub>4</sub>
Mol. Wt.: 764.95

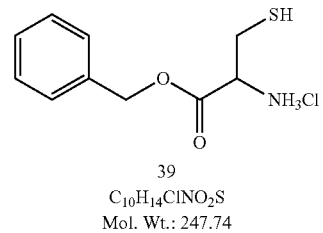

39
C<sub>10</sub>H<sub>14</sub>ClNO<sub>2</sub>S
Mol. Wt.: 247.74

A round bottomed flask charged with benzylester 38 (76.5g, 100 mmol) in CH$_2$Cl$_2$ (800 mL) was evaporated and refilled with nitrogen for several times. Dithiothreitol (38.6 g, 250 mmol) and NEt$_3$ (35 mL, 250 mmol) were added and the mixture was stirred for 1 h. The organic layer was washed with water (3×) and dried (MgSO₄). The solvent was removed and the residue dissolved in diethyl ether. The hydrochloride was precipitated by addition of a HCl-diethyl ether solution. After filtration the crude product was purified by crystallization from ethyl acetate to afford 39 (44.6 g, 90%).

¹H-NMR of 39-HCl (400 MHz, CDCl₃): δ=7.40-7.30 (m, 5H), 5.20 (d, J=12.3 Hz, 1H), 5.15 (d, J=12.3 Hz, 1H), 3.69 (dd, J=5.5, 5.1 Hz, 1H), 2.88 (dd, J=13.7, 5.8 Hz, 1H), 2.83 (dd, J=13.5, 4.3 Hz, 2H), 1.75 (br. s, 2H).

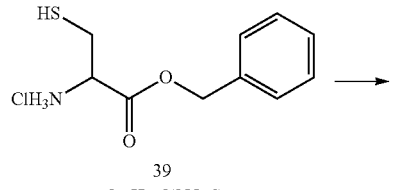

39
C₁₀H₁₄ClNO₂S
Mol. Wt.: 247.74

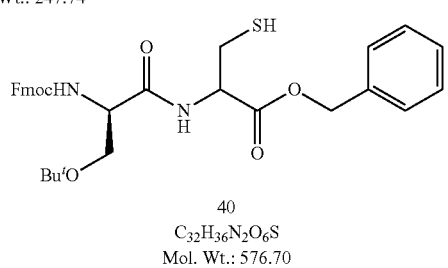

40
C₃₂H₃₆N₂O₆S
Mol. Wt.: 576.70

To a solution of cystein ester hydrochloride (3.10 g, 12.5 mmol) and Fmoc-D-Ser(tBu)-OH (3.83 g, 10 mmol) in CH₂Cl₂ (50 mL) were added HOBt (2.03 g, 15 mmol), EDC.HCl (2.88 g, 15 mmol) and DIPEA (2.2 mL, 12.5 mmol) successively. The mixture was stirred for 16 h, then sat. NaHCO₃ solution was added. The organic layer was washed with water (2×), dried (MgSO₄) and evaporated. The crude product was purified by chromatography (silica gel, DCM) to afford 40 (4.05 g, 70%).

¹H-NMR (400 MHz, CDCl₃): δ=7.77 (d, J=7.5 Hz, 2H), 7.60 (dd, J=7.5, 2.0 Hz, 2H), 7.56 (br. s, 1H), 7.40 (t, J=7.7 Hz, 2H) 7.35 (s, 5H), 7.32 (t, J=7.5 Hz, 2H), 5.75 (br. s, 1H), 5.26 (d, J=12.3 Hz, 1H), 5.20 (d, J=12.3 Hz, 1H), 4.91 (dt, J=7.5, 3.8 Hz, 1H), 4.40 (m, 2H), 4.30 (br. s, 1H), 4.24 (t, J=7.0 Hz, 1H), 3.83 (br. s, 1H), 3.43 (t, J=8.4 Hz, 1H), 3.09-2.96 (m, 2H), 1.23 (s, 9H).

¹³C-NMR (100 MHz, CDCl₃): δ=171.4, 170.0, 169.5, 156.0, 143.7, 141.3 (2C), 135.0, 128.7 (2C), 128.4, 127.7, 127.1, 125.1. 120.0, 75.8, 74.4, 67.6, 67.3, 67.2, 65.3, 64.4, 61.6, 54.7, 53.9, 47.1, 40.2, 32.6, 30.9, 30.4, 27.9, 26.7.

HRMS (ESI): C₃₂H₃₆N₂O₆NaS ([M+Na]⁺) requires 599.2192, found 599.2192.

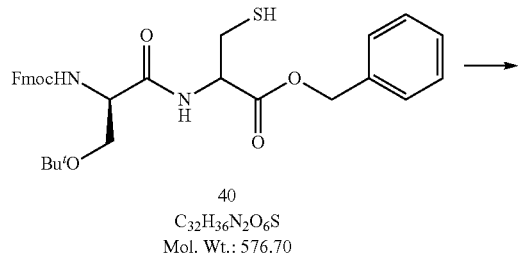

40
C₃₂H₃₆N₂O₆S
Mol. Wt.: 576.70

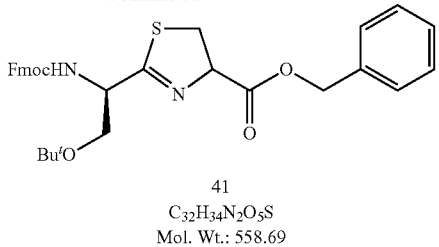

41
C₃₂H₃₄N₂O₅S
Mol. Wt.: 558.69

To a solution of PPh₃PO (1.085 g, 3.9 mmol) in CH₂Cl₂ (10 mL) was added triflic anhydride (0.32 mL, 1.95 mmol) at 0° C. The resulting mixture was stirred for 10 min at 0° C. and then cooled to −20° C. The dipeptide (750 mg, 1.3 mmol) in CH₂Cl₂ (3 mL) was added. The mixture was stirred for 30 min and then quenched by addition of sat. aq. NaHCO₃ solution. The organic layer was washed with water (2×), dried (MgSO₄) and evaporated. The crude product was purified by chromatography (CH₂Cl₂/acetone, 98:2) to afford 41 (555 mg, 76%).

[α]₅₈₉²⁰=30.3 (c=1.18, CHCl₃).

¹H-NMR (400 MHz, CDCl₃): δ=7.77 (d, J=7.5 Hz, 2H), 7.62 (m, 3H), 7.40 (t, J=7.7 Hz, 2H) 7.44-7.28 (m, 9H), 5.82 (d, J=7.2 Hz, 1H), 5.29-5.12 (m, 3H), 4.73 (br. s, 1H), 4.55 (dd, J=9.6, 7.5 Hz, 1H), 4.35 (m, 1H), 4.26 (m, 1H), 3.76 (m, 1H), 3.66-3.46 (m, 3H), 1.16 (s, 9H).

HRMS (ESI): C₃₂H₃₄N₂O₅NaS ([M+Na]⁺) requires 581.2086, found 581.2089.

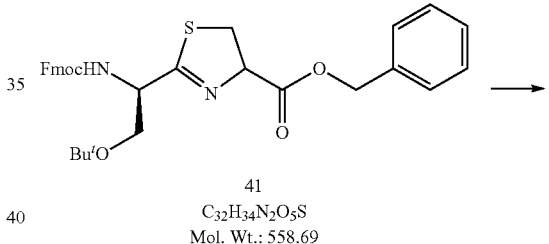

41
C₃₂H₃₄N₂O₅S
Mol. Wt.: 558.69

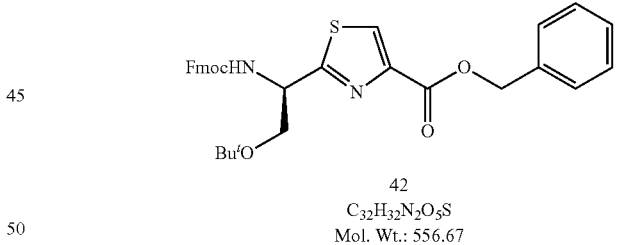

42
C₃₂H₃₂N₂O₅S
Mol. Wt.: 556.67

To a solution of thiazoline (519 mg, 0.93 mmol) in CH₂Cl₂ (9.3 mL) was added MnO₂ (1.61 g, 18.6 mmol). The mixture was stirred for 24 h at r.t. After filtration through celite the crude product was purified by chromatography (CH₂Cl₂/acetone, 97:3) to afford thiazole (352 mg, 68%).

[α]₅₂₉²⁰=−0.88 (c=1.13, CHCl₃).

¹H-NMR (400 MHz, CDCl₃): δ=8.10 (s, 1H), 7.76 (br. s, 2H), 7.62 (br. s, 2H), 7.50-7.27 (m, 9H), 5.95 (br. s, 1H), 5.40 (m, 2H), 5.21 (br. s, 1H), 4.55-4.37 (m, 2H), 4.25 (br. s, 1H), 3.90 (br. s, 1H), 3.69 (dd, J=8.5, 4.8 Hz, 1H), 1.12 (s, 9H).

¹³C-NMR (100 MHz, CDCl₃): δ=172.1, 161.1, 158.8, 146.5, 143.8, 141.3, 135.7, 128.6, 128.4 (2C), 127.9, 127.7, 127.0, 125.0. 120.0, 77.2, 73.9, 67.1, 66.9, 63.5, 54.0, 47.2, 27.3.

HRMS (ESI): $C_{32}H_{32}N_2O_5NaS$ ([M+Na]$^+$) requires 579.1930, found 579.1909.

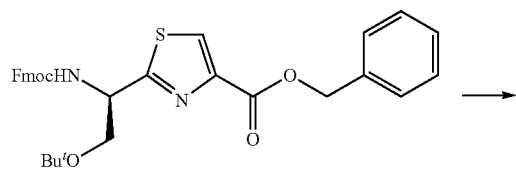

42
$C_{32}H_{32}N_2O_5S$
Mol. Wt.: 556.67

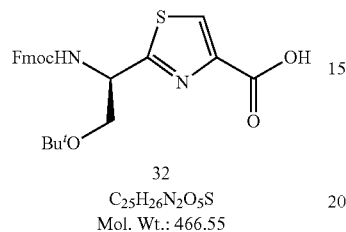

32
$C_{25}H_{26}N_2O_5S$
Mol. Wt.: 466.55

To a solution of thiazole (151 mg, 0.27 mmol) in THF (2 mL) and MeOH (2 mL) was added $HCO_2NH_4$ (81 mg, 0.3 g/mmol) and Pd/C (10%, 81 mg, 0.3 g/mmol). The mixture was stirred for 8 h at r.t. After filtration through celite the crude product was purified by chromatography ($CH_2Cl_2$/MeOH, 9:1) to afford the acid (90, 71%).

$[\alpha]_{589}^{20}$=13 (c=1.05, MeOH).

$^1$H-NMR (400 MHz, CDCl$_3$): δ=8.10 (s, 1H, 7.76 (br. s, 2H), 7.62 (br. s, 2H), 7.50-7.27 (m, 9H), 5.95 (br. s, 1H), 5.40 (m, 2H), 5.21 (br. s, 1H), 4.55-4.37 (m, 2H), 4.25 (br. s, 1H), 3.90 (br. s, 1H), 3.69 (dd, J=8.5, 4.8 Hz, 1H), 1.12 (s, 9H).

$^{13}$C-NMR (100 MHz, CDCl$_3$): δ=172.1, 161.1, 158.8, 146.5, 143.8, 141.3, 135.7, 128.6, 128.4 (2×), 127.9, 127.7, 127.0, 125.0. 120.0, 77.2, 73.9, 67.1, 66.9, 63.5, 54.0, 47.2, 27.3.

HRMS (ESI): $C_{32}H_{32}N_2O_5NaS$ ([M+Na]$^+$) requires 489.1460, found 489.1465.

3. Synthesis of Argyrin and Respective Derivatives

In the new route according to the invention, the double bond is established early in the synthesis. The dehydroalanine unit is installed after coupling of the amino acids D-alanine and D/L-serine. Treatment with CuCl and EDC furnished dipeptide 20 in high yield, which can be converted after coupling with ethyl sarcosine to tripeptide 14.

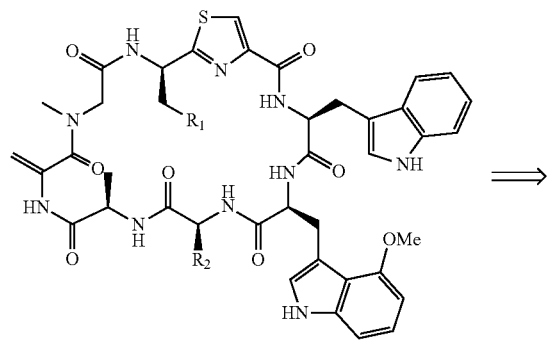

Argyrin A, (2): $R_1$ = H, $R_2$ = H
Argyrin F (3): $R_1$ = OH, $R_2$ = H
Derivative 4: $R_1$ = OH, $R_2$ = $CH_3$ (L)
Derivative 5: $R_1$ = OH, $R_2$ = $CH_3$ (D)

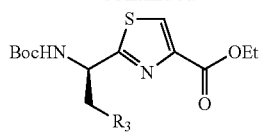

12: $R_3$ = H
13: $R_3$ = OtBu

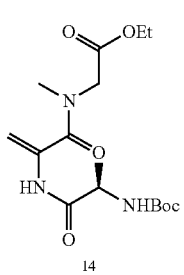

14

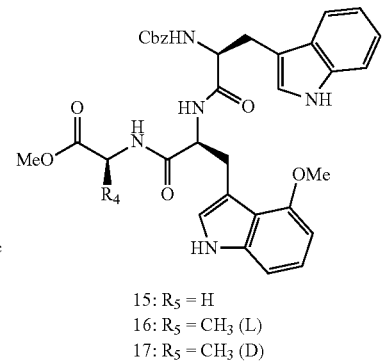

15: $R_5$ = H
16: $R_5$ = $CH_3$ (L)
17: $R_5$ = $CH_3$ (D)

Fragment 12 is synthesized following literature known procedures according to Ley. Our new, efficient and economic synthesis method to 4-Methoxytryptophane allowed us the synthesis on multi gram scale. Peptide couplings with L-tryptophane and glycine or alanine accessed tripeptides 15-17.

3.1 Synthesis of the Fragments (12-17)

3.1.1 Synthesis of Fragment 14

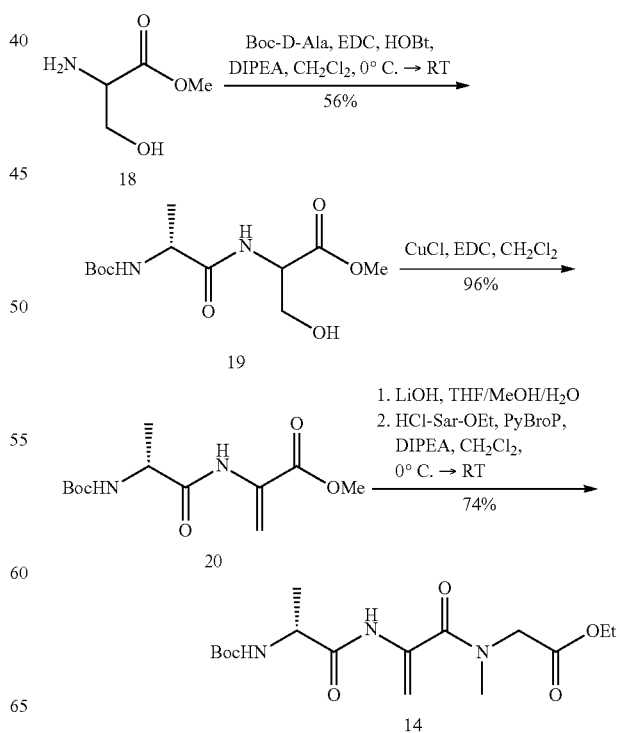

N-Boc-D-Ala-Ser-OMe (19)

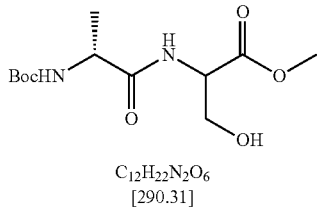

C$_{12}$H$_{22}$N$_2$O$_6$
[290.31]

1-Hydroxybenzotriazole (1.30 g, 9.6 mmol), EDC (1.66 g, 8.7 mmol) and Diisopropylethylamine (1.21 mL, 7.1 mmol) were added successively to a suspension of D/L-Ser-OMe.HCl (1.00 g, 6.4 mmol) and Boc-D-Ala-OH (1.46 g, 7.7 mmol) in dichloromethane (5 mL) at 0° C. under argon. The reaction mixture was warmed to room temperature and stirred for 4 hours. The solution was partitioned between aqueous 1 N KHSO$_4$ (10 mL) and dichloromethane (10 mL). The aqueous layer was extracted with dichloromethane (2×10 mL). The combined organic layers were washed with aqueous saturated NH$_4$Cl and dried over Na$_2$SO$_4$. Removal of the solvent under reduced pressure and subsequent purification by column chromatography (dichloromethane with a gradient of 3 to 5% of methanol) gave 19 as a colourless sticky solid (1.05 g, 3.6 mmol, 56%).

R$_f$=0.28 (Ethyl acetate)

$^1$H-NMR (400 MHz, CDCl$_3$): δ=7.25-7.17 (m, 1 H), 5.43-5.23 (m, 1 H), 4.69-4.55 (m, 1 H), 4.25-4.13 (m, 1 H), 3.98-3.89 (m, 2 H), 3.76 (s, 3 H), 1.44-1.40 (m, 9 H), 1.36 (d, J=6.8 Hz, 3 H).

HRMS (ESI) calculated for C$_{12}$H$_{22}$N$_2$O$_6$ ([M+Na]$^+$): 313.1376, f found: 313.1376.

N-Boc-D-Ala-DHA-OMe (20)

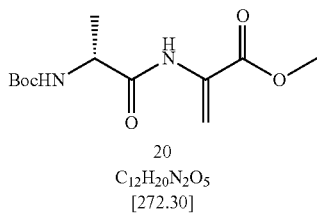 [SMILES: C=C(NC(=O)[C@@H](C)NC(=O)OC(C)(C)C)C(=O)OC]

C$_{12}$H$_{20}$N$_2$O$_5$
[272.30]

CuCl (31 mg, 0.31 mmol) and EDC (1.19 g, 6.18 mmol) were added to a solution of N-Boc-D-Ala-Ser-OMe 19 (897 mg, 3.09 mmol) in dichloromethane (40 mL) at room temperature under argon. The reaction mixture was stirred for 16 hours, filtered through Celite® and washed with brine. The organic layer was dried over Na$_2$SO$_4$. Removal of the solvent under reduced pressure and subsequent purification by column chromatography (dichloromethane with 3% methanol) gave 20 as a yellow solid (808 mg, 2.97 mmol, 96%).

R$_f$=0.57 (Dichloromethane with 4% methanol).

[α]$_D^{20}$=55.9 (c=1.17, CHCl$_3$).

$^1$H-NMR (400 MHz, CDCl$_3$): δ=8.45 (br. s, 1 H), 6.57 (s, 1 H), 5.88 (m, 1 H), 5.11-5.01 (m, 1 H), 4.31-4.18 (m, 1 H), 3.82 (s, 3 H), 1.43 (s, 9 H), 1.38 (d, J=6.8 Hz, 3 H).

$^{13}$C-NMR (100 MHz, CDCl$_3$): δ=171.68, 164.36, 155.58, 130.96, 109.32, 80.56, 53.04, 51.04, 28.37, 18.05.

HRMS (ESI) calculated for C$_{12}$H$_{20}$N$_2$O$_5$Na ([M+Na]$^+$): 295.1270, found: 295.1273.

N-Boc-D-Ala-DHA-Sar-OEt (14)

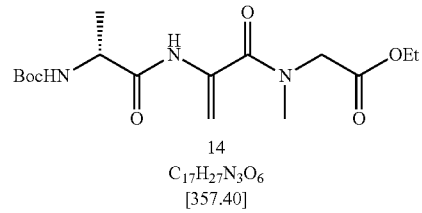 [SMILES: C=C(NC(=O)[C@@H](C)NC(=O)OC(C)(C)C)C(=O)N(C)CC(=O)OCC]

C$_{17}$H$_{27}$N$_3$O$_6$
[357.40]

A 0.5 N aqueous solution of LiOH (1.04 mL, 0.52 mmol) was added dropwise to a solution of N-Boc-D-Ala-DHA-Sar-OEt (20) (129 mg, 0.47 mmol) in tetrahydrofurane/methanol/water (4:1:2 mL) at 0° C. The reaction mixture was warmed to room temperature and stirred for 2 hours. The solution was partitioned between 0.1 N KHSO$_4$ (10 mL) and dichloromethane (10 mL). The aqueous layer was extracted with dichloromethane (2×10 mL). The combined organic layers were dried over Na$_2$SO$_4$ and the solvent was removed under reduced pressure.

To a solution of the residue in dichloromethane (5 mL) at 0° C. under argon were added successively HCl-Sar-OEt (109 mg, 0.71 mmol), PyBroP (331 mg, 0.71 mmol) and dropwise Diisopropylethylamine (24.3 µL, 1.42 mmol). The reaction mixture was warmed to room temperature and stirred for 19 hours. The solution was partitioned between aqueous saturated NH$_4$Cl (10 mL) and dichloromethane (10 mL). The aqueous layer was extracted with dichloromethane (2×10 mL) and the combined organic layers were dried over Na$_2$SO$_4$. Removal of the solvent and subsequent purification by column chromatography (ethyl acetate) gave 14 as a colourless sticky solid (124 mg, 0.35 mmol, 74%).

R$_f$=0.38 (Ethyl acetate).

[α]$_D^{20}$=16.8 (c=1, acetone).

$^1$H-NMR (400 MHz, CDCl$_3$): δ=8.34 (br. s, 1 H), 6.10-5.58 (m, 1 H), 5.23-4.86 (m, 2 H), 4.29-4.09 (m, 5 H), 3.28-2.92 (m, 3 H), 1.43 (s, 9 H), 1.36 (d, J=6.8 Hz, 3 H), 1.27 (t, J=7.2 Hz, 3 H).

$^{13}$C-NMR (100 MHz, CDCl$_3$): δ=171.7, 168.9, 168.0, 155.7, 134.6, 105.0, 80.5, 61.5, 50.6, 49.5, 39.0, 28.4, 18.2, 14.3 ppm.

HRMS (ESI) calculated for C$_{16}$H$_{27}$N$_3$O$_6$Na ([M+Na]$^+$): 380.1789, found: 380.1789.

3.1.2 Synthesis of the Thiazole 13

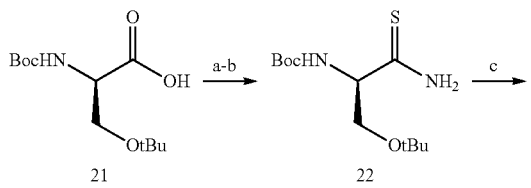

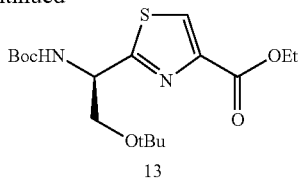

13

Thioamide 22

DCC (59 mg, 0.29 mmol) was added to a suspension of N-Boc-(O-tBu)-D-serine (100 mg, 0.23 mmol) and 1-hydroxybenzotriazole (31 mg, 0.23 mmol) in dichloromethane (3 mL) at 0° C. The solution was warmed to room temperature and stirred for 1 hour. The solution was cooled to 0° C. and ammonia (0.06 mL) in dichloromethane (0.3 mL) was added. The reaction mixture was stirred at 0° C. for 1 hour and then filtered. The mother liquor was concentrated and purified by column chromatography (dichloromethane/acetone, 4:1) to give the amide as a white solid (41 mg, 70%).

$[\alpha]_{589}^{20}=-51.47$ (c=1.02, CHCl$_3$).

$^1$H-NMR (400 MHz, CDCl$_3$): δ=6.59 (br s, 1 H), 6.07 (br s, 1 H), 5.43 (br s, 1 H), 4.19-4.04 (m, 1 H), 3.77-3.67 (m, 1 H), 3.34 (t, J=7.7 Hz, 1 H), 1.40 (s, 9 H), 1.15 (s, 9 H).

$^{13}$C-NMR (100 MHz, CDCl$_3$): δ=173.4, 155.4, 79.8, 73.9, 61.7, 54.0, 28.2, 27.3.

HRMS (ESI) calculated for $C_{14}H_{27}N_3O_4Na$ ([M+Na+CH$_3$CN]$^+$): 324.1899, found 324.1895.

Belleau's reagent (5.3 g, 10.1 mmol) was added to a solution of the amide (4.4 g, 16.8 mmol) in tetrahydrofurane (250 mL) at 0° C. The solution was warmed to room temperature, stirred for 90 minutes and partitioned between ice (250 mL) and saturated aqueous NaHCO$_3$ (250 mL). This was extracted with methyl tert-butyl ether (3×250 mL), the organic layers were combined, washed with brine (250 mL), dried (MgSO$_4$) and concentrated. The residue was purified by column chromatography (dichloromethane/ethyl acetate, 5:1) to give thioamide 22 as colourless oil (3.8 g, 82%).

$[\alpha]_{589}^{20}=-74.50$ (c=1.03, CHCl$_3$).

$^1$H-NMR (400 MHz, CDCl$_3$): δ=7.93 (br s, 1 H), 7.53 (br s, 1 H), 5.65 (br s, 1 H), 4.40 (dt, J=6.8, 3.9 Hz, 1 H), 3.82 (dd, J=8.8, 3.9 Hz, 1 H), 3.44 (br s, 1 H), 1.44 (s, 9 H), 1.17 (s, 9 H).

$^{13}$C-NMR (100 MHz, CDCl$_3$): δ=207.0, 155.1, 80.3, 74.1, 63.9, 59.6, 28.3, 27.4.

HRMS (ESI) calculated for $C_{12}H_{24}N_2O_3S$ ([M]$^+$): 276.1508, found 276.1506.

Thiazole 13

Ethyl bromopyruvate (4.5 mL, 37.9 mmol) was added to a suspension of KHCO$_3$ (10.3 g, 102.9 mmol) and thioamide 22 (3.6 g, 12.8 mmol) which had been stirred in 1,2-dimethoxyethane (30 mL) at −15° C. for 5 minutes. After 1 minute, the mixture was treated with a solution of 2,6-lutidine (12.7 mL, 109.1 mmol) and trifluoroacetic anhydride (2.7 g, 12.7 mmol) in 1,2-dimethoxyethane (20 mL) at −15° C. The reaction mixture was stirred for 3 hours at the same temperature, poured into water (90 mL) and extracted with dichloromethane. The organic layers were combined, dried (MgSO$_4$) and concentrated. The residue was purified by column chromatography (dichloromethane/ethyl acetate, 8:1) to give thiazole 13 as a yellow solid (3.7 g, 77%).

$[\alpha]_{598}^{20}=14.21$ (c=1.10, CHCl$_3$).

$^1$H-NMR (400 MHz, CDCl$_3$): δ=8.06 (s, 1 H), 5.67 (br s, 1 H), 5.10 (br s, 1 H), 4.41-4.26 (m, 2 H), 3.88-3.85 (m, 1 H), 3.69-3.61 (m, 1 H), 1.44 (s, 9 H), 1.37 (t, J=7.0 Hz, 3 H), 1.07 (s, 9 H).

$^{13}$C-NMR (100 MHz, CDCl$_3$): δ=161.4, 155.2, 146.8, 127.4, 80.2, 73.8, 63.5, 61.3, 55.1, 53.6, 28.3, 27.3, 14.3.

HRMS (ESI): $C_{17}H_{28}N_2O_5S$ ([M$^+$) requires 372.1719, found 372.1720.

3.2 Modified Synthesis of Argyrin A (2)

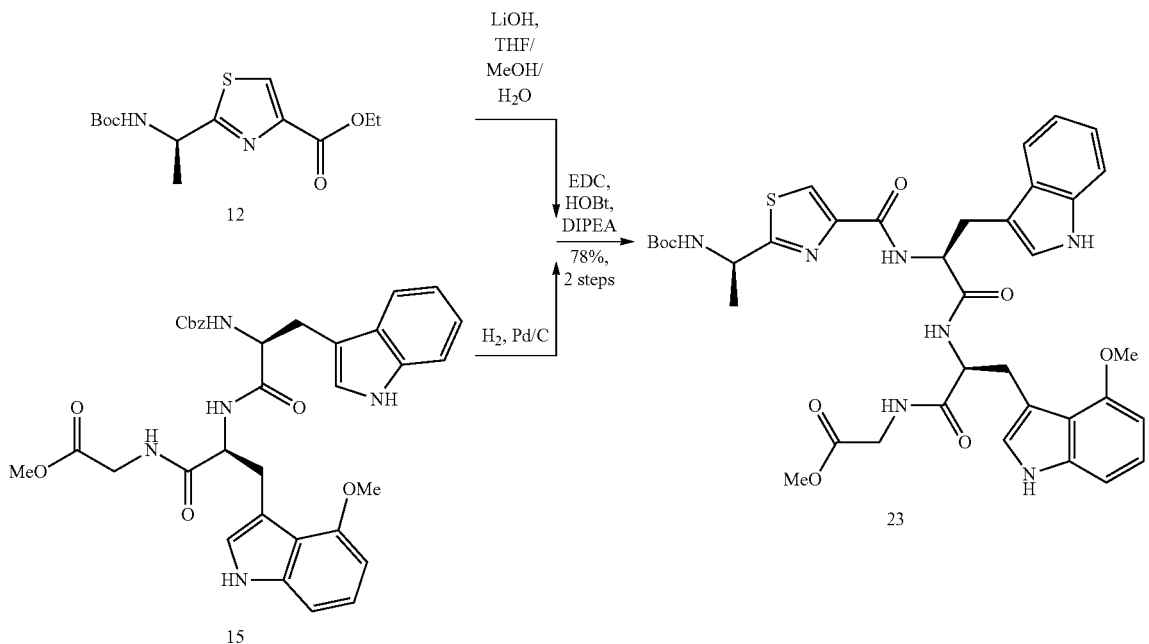

-continued

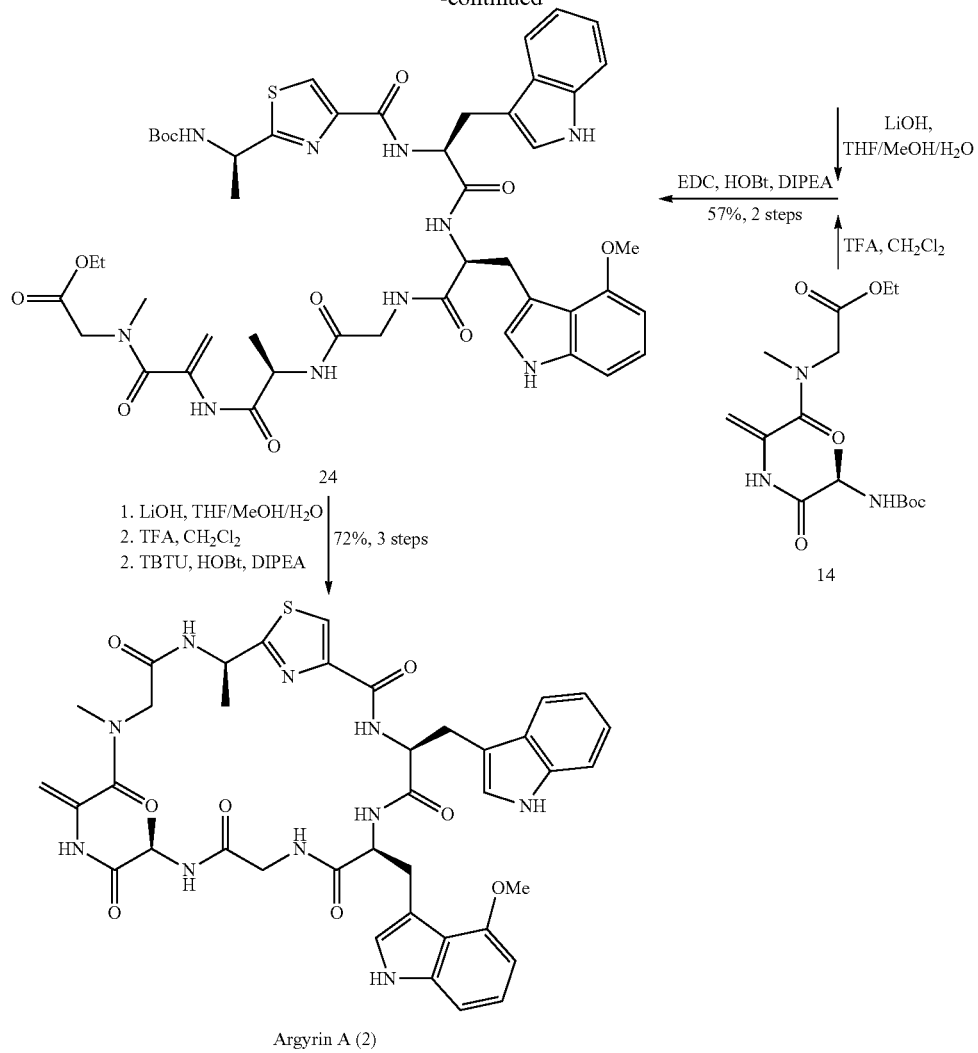

Argyrin A (2)

N$^\alpha$-Boc-D-AlaThz-Trp-(4-OMe)Trp-Gly-OMe (23)

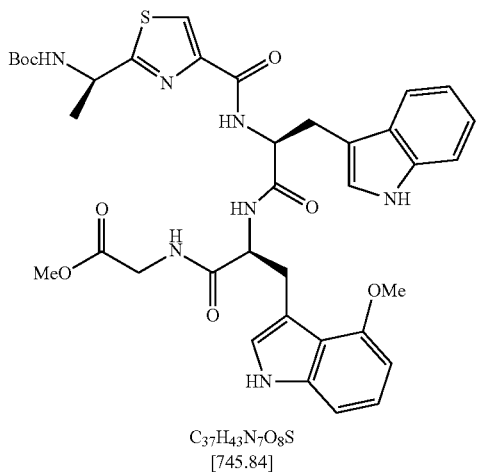 [SMILES: COC(=O)CNC(=O)[C@H](Cc1c[nH]c2cccc(OC)c12)NC(=O)[C@H](Cc1c[nH]c2ccccc12)NC(=O)c1csc([C@@H](C)NC(=O)OC(C)(C)C)n1]

C$_{37}$H$_{43}$N$_7$O$_8$S
[745.84]

A 0.5 N aqueous solution of LiOH (1.5 mL, 0.74 mmol) was added to a solution of thiazole 12 (183 mg, 0.61 mmol) in tetrahydrofurane/methanol/water (7.4:1.8:3.7 mL) at 0° C. The reaction mixture was warmed to room temperature and stirred for 1.5 hours. The solution was partitioned between 0.1 N aqueous HCl (20 mL) and dichloromethane (40 mL). The aqueous layer was extracted with dichloromethane (2×10 mL) and the organic layers were combined, dried (Na$_2$SO$_4$) and concentrated. The resulting carboxylic acid was used directly in the next step.

Palladium on charcoal (30 mg, 10% weight) was added to a solution of N$^\alpha$-Cbz-Trp-(4-OMe)Trp-Gly-OMe 15 (300 mg, 0.48 mmol) in methanol (30 mL). The reaction mixture was purged with hydrogen three times and stirred for 4 hours at room temperature. The suspension was filtered through a plug of Celite®, washed with methanol (2×20 mL) and concentrated by coevaporation with toluene (2×20 mL). The amine was used directly in the next step.

EDC (113 mg, 0.59 mmol) was added successively to a suspension of the carboxylic acid, the amine and 1-hydroxybenzotriazole (97 mg, 0.72 mmol) in dichloromethane (20 mL) at 0° C. The reaction mixture was warmed to room temperature and stirred for 18 hours. The solution was partitioned between water (10 mL) and dichloromethane (10 mL). The aqueous layer was extracted with dichloromethane (2×10 mL). The organic layers were combined, dried (Na$_2$SO$_4$) and concentrated. The residue was purified by column chromatography (dichloro-methane with 6% methanol) to give pentapeptide 23 as a colorless solid (280 mg, 0.38 mmol, 78%).

$[\alpha]_{589}^{20}=-47.39$ (c=1.11, CHCl$_3$).

$^1$H-NMR (400 MHz, CDCl$_3$): δ=8.81 (br, 1 H), 7.92 (s, 1 H), 7.79 (br, 1 H), 7.66-7.59 (m, 1 H), 7.55 (d, J=7.9 Hz, 1 H), 7.28 (d, J=7.9 Hz, 1 H), 7.15 (t, J=7.5 Hz, 1 H), 7.09-7.03 (m, 2 H), 6.98-6.90 (m, 3 H), 6.62-6.52 (m, 2 H), 6.40 (d, J=7.5 Hz, 1 H), 5.15 (d, J=7.2 Hz, 1 H), 4.93-4.85 (m, 2 H), 4.05 (dd, J=17.9, 6.0 Hz, 1 H), 3.88-3.79 (m, 1 H), 3.71 (s, 3 H), 3.68 (s, 3 H), 3.46 (dd, J=14.7, 4.4 Hz, 1 H), 3.17-3.07 (m, 3 H), 1.51-1.43 (m, 12 H).

$^{13}$C-NMR (100 MHz, CDCl$_3$): δ=175.0, 172.1, 171.7, 170.3, 161.6, 155.2, 154.0, 148.9, 138.2, 136.2, 127.4, 123.7, 123.2, 122.7, 122.6, 122.2, 119.7, 118.7, 117.5, 111.5, 110.2, 109.7, 105.4, 99.8, 81.0, 55.5, 55.4, 54.9, 52.3, 49.3, 41.2, 28.5, 28.1, 26.7, 21.9.

HRMS (ESI) calculated for C$_{37}$H$_{43}$N$_7$O$_8$NaS ([M+Na]$^+$): 768.2792, found: 768.2798.

N-Boc-D-AlaThz-Trp-(4-OMe)Trp-Gly-D-Ala-DHA-Sar-OEt (24)

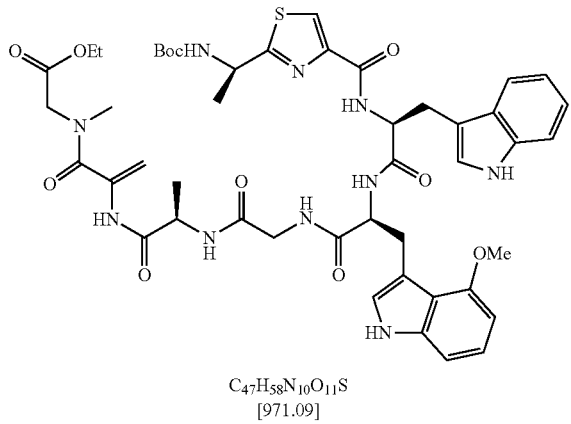 [SMILES: C=C(NC(=O)[C@@H](C)NC(=O)CNC(=O)[C@H](Cc1c[nH]c2cccc(OC)c12)NC(=O)[C@H](Cc1c[nH]c2ccccc12)NC(=O)c1csc([C@@H](C)NC(=O)OC(C)(C)C)n1)C(=O)N(C)CC(=O)OCC]

C$_{47}$H$_{58}$N$_{10}$O$_{11}$S
[971.09]

A 0.5 N aqueous solution of LiOH (0.22 mL, 0.10 mmol) was added to a solution of ester 23 (69 mg, 0.09 mmol) in tetrahydrofurane/methanol/water (2.9:0.7:1.4 mL) at 0° C. The reaction mixture was warmed to room temperature and stirred for 1 hour. The solution was partitioned between 0.1 N aqueous HCl (2.2 mL) and dichloromethane (4.3 mL). The aqueous layer was extracted with dichloromethane (2×3 mL) and the organic layers were combined, dried (Na$_2$SO$_4$) and concentrated. The resulting carboxylic acid was used directly in the next step.

Trifluoroacetic acid (1.4 mL) was added dropwise to a solution of carbamate 14 (57 mg, 0.16 mmol) in dichloromethane (3 mL) at 0° C. The reaction mixture was warmed to room temperature and stirred or 30 minutes. The solution was concentrated by coevaporation with toluene (3×3 mL) and the resulting ammonium salt was used directly in the next step.

Diisopropylethylamine (30 μL, 0.15 mmol) and EDC (32 mg, 0.17 mmol) were added successively to a suspension of the carboxylic acid, the amine and 1-hydroxybenzotriazole (29 mg, 0.21 mmol) in dichloromethane (10 mL) at 0° C. The reaction mixture was warmed to room temperature and stirred for 18 hours. The solution was partitioned between 0.1 N aqueous HCl (6 mL) and dichloromethane (12 mL). The aqueous layer was extracted with dichloromethane (2×5 mL). The organic layers were combined, washed with aqueous saturated ammonium chloride (10 mL), dried (Na$_2$SO$_4$) and concentrated. The residue was purified by column chromatography (dichloromethane with 5% methanol) to give octapeptide 24 as a sticky solid (105 mg, 0.11 mmol, 81%).

$[\alpha]_{589}^{20}=49.7$ (c=2.09, CHCl$_3$).

HRMS (ESI) calculated for C$_{47}$H$_{58}$H$_{10}$O$_{11}$NaS ([M+Na]$^+$): 993.3905, found: 993.3907.

Argyrin A (2)

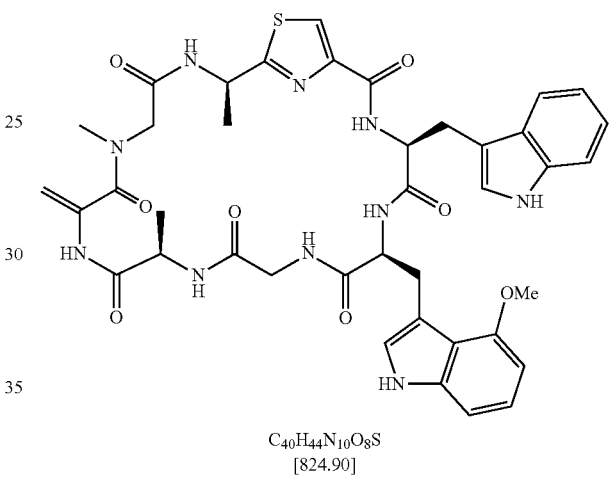

C$_{40}$H$_{44}$N$_{10}$O$_8$S
[824.90]

A 0.5 N aqueous solution of LiOH (0.27 mL, 0.11 mmol) was added to a solution of ester 24 (100 mg, 0.10 mmol) in tetrahydrofurane/methanol/water (3.7:0.7:2 mL) at 0° C. The reaction mixture was warmed to room temperature and stirred for 2 hours. The solution was partitioned between 0.1 N aqueous HCl (7 mL) and dichloromethane (14 mL). The aqueous layer was extracted with dichloromethane (2×10 mL) and the organic layers were combined, dried (Na$_2$SO$_4$) and concentrated. The resulting carboxylic acid was used directly in the next step.

Trifluoroacetic acid (7.3 mL) was added dropwise to a solution of the carboxylic acid in dichloromethane (5 mL) at 0° C. The reaction mixture was warmed to room temperature and stirred for 1 hour. The solution was concentrated by coevaporation with toluene (3×10 mL) and the resulting ammonium salt was used directly in the next step.

Diisopropylethylamine (70 μL, 0.21 mmol) and TBTU (66 mg, 0.40 mmol) were added successively to a solution of the linear peptide and 1-hydroxybenzotriazole (28 mg, 0.21 mmol) in dichloromethane (170 mL) at room temperature. The reaction mixture was stirred for 18 hours. The reaction mixture was concentrated under reduced pressure. The residue was purified by column chromatography (dichloromethane with 4% methanol) to give argyrine A (2) as a sticky solid (47 mg, 0.06 mmol, 57%).

[α]$_{589}^{20}$=145.2 (c=0.91, CHCl$_3$).
$^1$H-NMR (400 MHz, CDCl$_3$): δ=10.69 (s, 1 H), 9.49 (s, 1 H), 8.84 (d, J=8.5 Hz, 1 H), 8.78 (d, 1.2 Hz, 1 H), 8.57 (d, J=7.2 Hz, 1 H), 8.38 (d, J=1.8 Hz, 1 H), 8.06 (s, 1 H), 7.36-7.32 (m, 2 H), 7.05 (d, J=8.1 Hz, 1 H), 6.96 (d, J=2.4 Hz, 1 H), 6.92-6.89 (m, 1 H), 6.89-6.85 (m, 2 H), 6.83 (d, J=2.2 Hz, 1 H), 6.33 (t, J=7.4 Hz, 1 H), 5.51-5.44 (m, 1 H), 5.37 (d, J=7.9 Hz, 1 H), 5.09-5.04 (m, 1 H), 5.01 (d, J=1.4 Hz, 1 H), 4.95 (d, J=16.9 Hz, 1 H), 4.72 (d, J=1.0 Hz, 1 H), 4.54-4.49 (m, 1 H), 4.34 (s, 3 H), 4.26-4.20 (m, 2 H), 3.57-3.46 (m, 3 H), 3.40 (d, J=16.9 Hz, 1 H), 3.32 (dd, J=14.9, 4.0 Hz, 1 H), 3.11 (s, 3 H), 2.84 (dd, J=15.2, 3.1 Hz, 1 H), 1.73 (d, J=7.2 Hz, 3 H), 1.42 (d, J=7.0 Hz, 3 H), 1.05 (dd, J=17.4, 5.1 Hz, 1 H).
$^{13}$C-NMR (100 MHz, CDCl$_3$): δ=172.9, 171.0, 170.8, 170.0, 169.8, 168.3, 166.8, 159.8, 152.3, 150.4, 138.3, 136.7, 134.7, 126.5, 125.5, 123.7, 123.6, 122.9, 121.2, 119.2, 117.3, 115.9, 111.3, 108.3, 106.6, 105.7, 101.2. 99.7, 57.7, 56.1, 52.1, 51.0, 48.3, 45.2, 40.4, 37.4, 26.9, 26.6, 20.3, 13.9.
HRMS (ESI) calculated for C$_{40}$H$_{45}$N$_{10}$O$_8$S ([M]$^+$): 825.3143, found: 825.3141.
3.3 Modified Synthesis for Argyrin F (3)
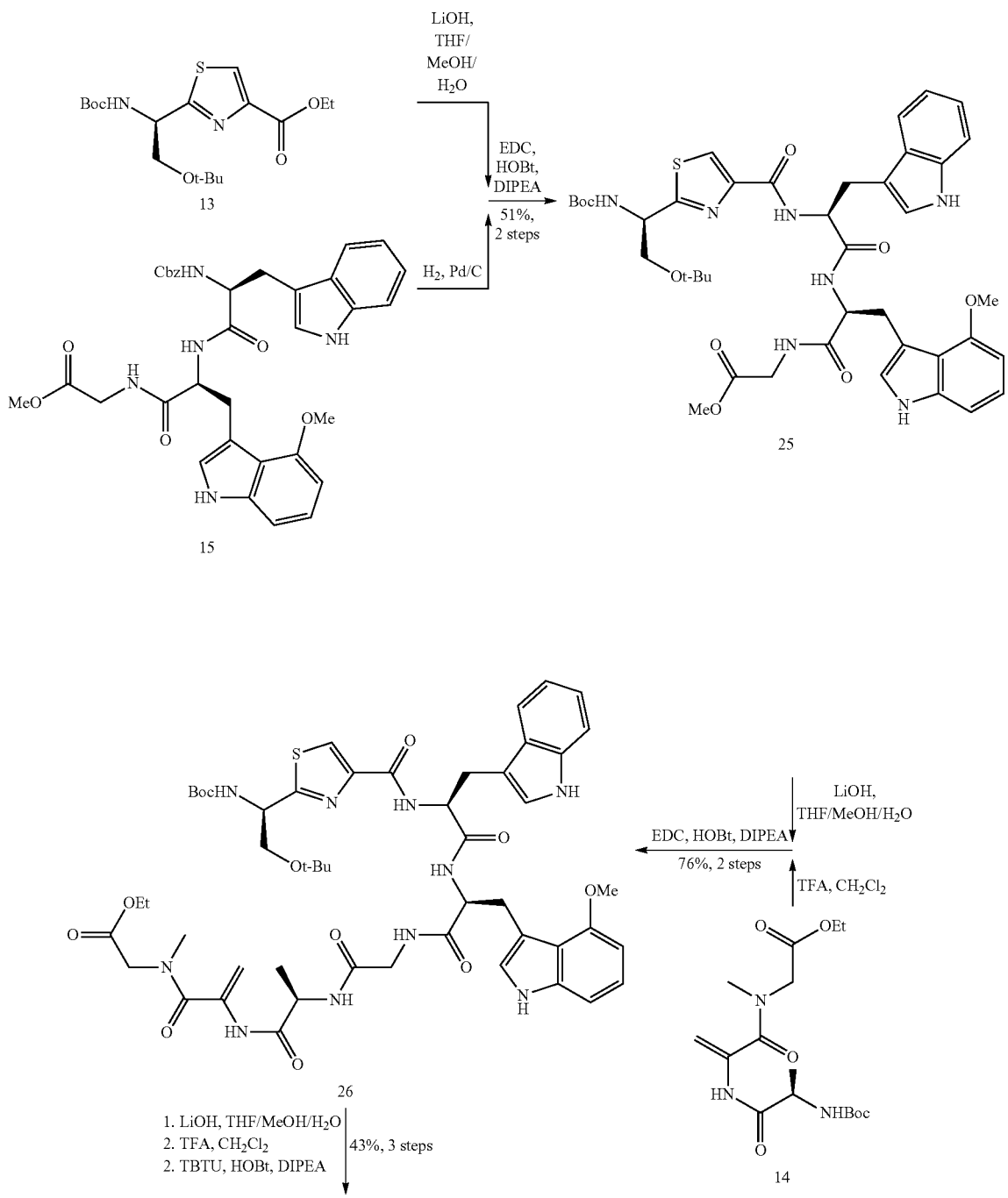

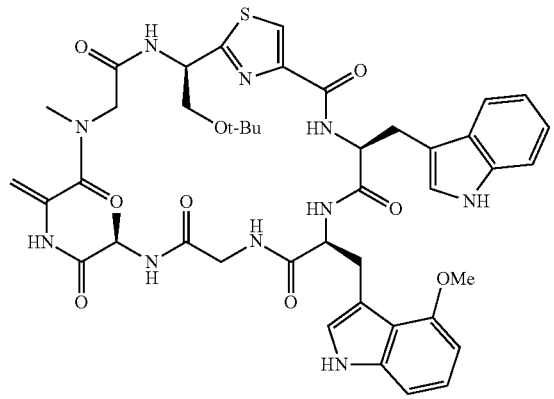

27

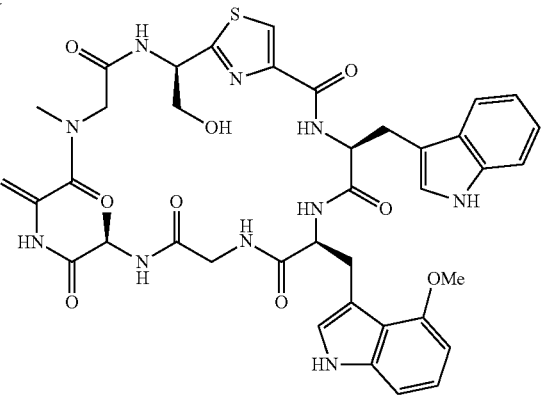

Argyrin F (3)

N$^\alpha$-Boc-D-SerThz-Trp-(4-OMe)Trp-Gly-OMe (25)

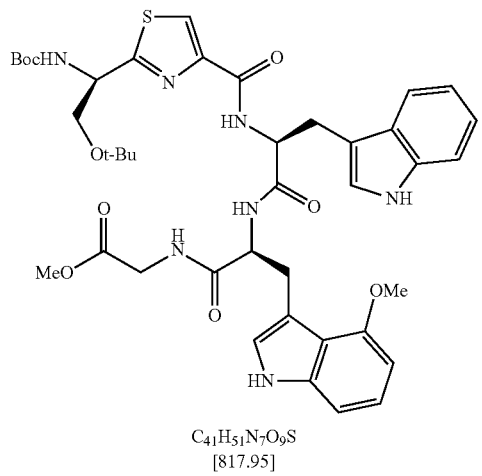 [SMILES: COC(=O)CNC(=O)[C@H](Cc1c[nH]c2cccc(OC)c12)NC(=O)[C@H](Cc1c[nH]c2ccccc12)NC(=O)c1csc([C@@H](COC(C)(C)C)NC(=O)OC(C)(C)C)n1]

C$_{41}$H$_{51}$N$_7$O$_9$S
[817.95]

A 0.5 N aqueous solution of LiOH (0.3 mL, 0.15 mmol) was added to a solution of thiazole 13 (46 mg, 0.13 mmol) in tetrahydrofurane/methanol/water (1.6:0.4:0.8 mL) at 0° C. The reaction mixture was warmed to room temperature and stirred for 3 hours. The solution was partitioned between 0.1 N aqueous HCl (5 mL) and dichloromethane (10 mL). The aqueous layer was extracted with dichloromethane (2×5 mL) and the organic layers were combined, dried (Na$_2$SO$_4$) and concentrated. The resulting carboxylic acid was used directly in the next step.

Palladium on charcoal (6 mg, 10% weight) was added to a solution of N$^\alpha$-Cbz-Trp-(4-OMe)Trp-Gly-OMe 15 (60 mg, 0.10 mmol) in methanol (3 mL). The reaction mixture was purged with hydrogen three times and stirred for 2 h at room temperature. The suspension was filtered through a plug of Celite®, washed with methanol (2×5 mL) and concentrated by coevaporation with toluene (2×5 mL). The amine was used directly in the next step.

EDC (23 mg, 0.12 mmol) was added successively to a suspension of the carboxylic acid, the amine and 1-hydroxybenzotriazole (19 mg, 0.14 mmol) in dichloromethane (3 mL) at 0° C. The reaction mixture was warmed to room temperature and stirred for 16 hours. The solution was partitioned between water (5 mL) and dichloromethane (5 mL). The aqueous layer was extracted with dichloromethane (2×5 mL). The organic layers were combined, washed with aqueous saturated ammonium chloride (10 mL), dried (Na$_2$SO$_4$) and concentrated. The residue was purified by column chromatography (dichloromethane with 4.5% methanol) to give pentapeptide 25 as a colourless solid (40 mg, 0.05 mmol, 78%).

$^1$H-NMR (400 MHz, CDCl$_3$): δ=9.03 (br, 1 H), 8.09 (br, 1 H), 7.93 (s, 1 H), 7.54 (m, 1 H), 7.52 (m, 1 H), 7.27 (m, 1 H), 7.13 (m, 1 H), 7.10 (m, 2 H), 6.95 (m, 2 H), 6.59 (m, 2 H), 6.36 (m, 1 H), 5.65 (d, J=7.0 Hz, 1 H), 4.84 (m, 1 H), 4.66 (m, 2 H), 4.08 (dd, J=18.0, 6.0 Hz, 1 H), 3.85 (dd, J=18.0, 5.0 Hz, 1 H), 3.68 (s, 3 H), 3.64 (s, 3 H), 3.44 (m, 1 H), 3.00-3.20 (m, 3 H), 1.77 (s, 3 H), 1.53 (s, 2 H), 1.47 (s, 9 H), 1.46 (m, 3 H), 1.11 (s, 9 H).

$^{13}$C-NMR (100 MHz, CDCl$_3$): δ=173.3, 172.1, 171.7, 171.5, 170.3, 161.6, 157.9, 154.4, 148.4, 137.5, 136.5, 127.6, 124.1, 122.9, 122.7, 122.5, 122.1, 119.5, 118.6, 117.4, 111.4, 110.0, 109.6, 105.4, 99.5, 81.0, 74.2, 63.4, 55.4, 54.8, 53.8, 52.3, 41.2, 34.9, 32.9, 28.5, 28.3, 27.4.

HRMS (ESI) calculated for C$_{41}$H$_{51}$N$_7$O$_9$NaS ([M+Na]$^+$): 840.3368, found 840.3367.

N-Boc-D-SerThz-Trp-(4-OMe)Trp-Gly-D-Ala-DHA-Sar-OEt (26)

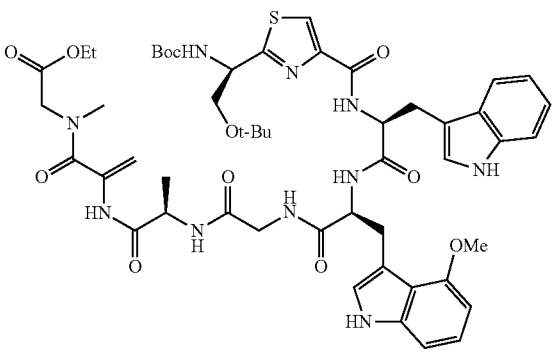

C$_{15}$H$_{66}$N$_{10}$O$_{12}$S
[1043.19]

A 0.5 N aqueous solution of LiOH (0.5 mL, 0.23 mmol) was added to a solution of ester 25 (120 mg, 0.15 mmol) in tetrahydrofurane/methanol/water (19.5:4.5:9.5 mL) at 0° C. The reaction mixture was warmed to room temperature and stirred for 3 hours. The solution was partitioned between 0.1 N aqueous HCl (40 mL) and dichloromethane (100 mL). The aqueous layer was extracted with dichloromethane (2×3 mL) and the organic layers were combined, dried (Na$_2$SO$_4$) and concentrated. The resulting carboxylic acid was used directly in the next step.

Trifluoroacetic acid (1.7 mL) was added dropwise to a solution of carbamate 14 (68 mg, 0.19 mmol) in dichloromethane (2.4 mL) at 0° C. The reaction mixture was warmed to room temperature and stirred or 3 hours. The solution was concentrated by coevaporation with toluene (3×5 mL) and the resulting ammonium salt was used directly in the next step.

Diisopropylethylamine (27 µL, 0.16 mmol) and EDC (35 mg, 0.18 mmol) were added successively to a suspension of the carboxylic acid, the amine and 1-hydroxybenzotriazole (32 mg, 0.23 mmol) in dichloromethane (12 mL) at 0° C. The reaction mixture was warmed to room temperature and stirred for 16 hours. The solution was partitioned between 0.1 N aqueous HCl (10 mL) and dichloromethane (20 mL). The aqueous layer was extracted with dichloromethane (2×10 mL). The organic layers were combined, washed with aqueous saturated ammonium chloride (20 mL), dried (Na$_2$SO$_4$) and concentrated. The residue was purified by column chromatography (dichloromethane with 5% methanol) to give octapeptide 26 as a sticky solid (119 mg, 0.11 mmol, 76%).

HRMS (ESI) calculated for C$_{51}$H$_{66}$N$_{10}$O$_{12}$NaS ([M+Na]$^+$): 1065.4480, found 1065.4470.

Macrocyclus (27)

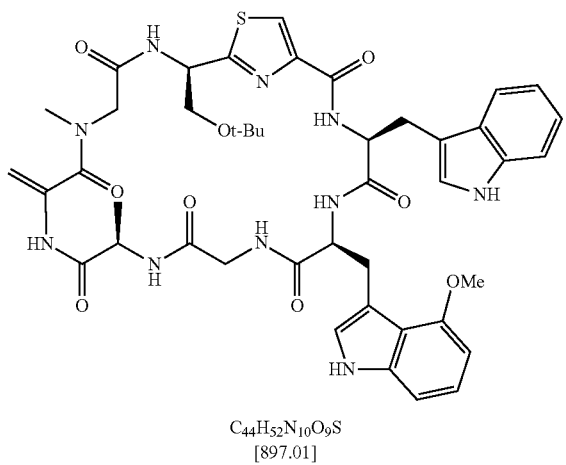 [SMILES: C=C1NC(=O)[C@@H](C)NC(=O)CNC(=O)[C@H](Cc2c[nH]c3cccc(OC)c23)NC(=O)[C@H](Cc2c[nH]c3ccccc23)NC(=O)c2csc(n2)[C@@H](COC(C)(C)C)NC(=O)CN(C)C1=O]

C$_{44}$H$_{52}$N$_{10}$O$_9$S
[897.01]

A 0.5 N aqueous solution of LiOH (2.5 mL, 0.13 mmol) was added to a solution of ester 26 (98 mg, 94 µmol) in tetrahydrofurane/methanol/water (4:1:2 mL) at 0° C. The reaction mixture was warmed to room temperature and stirred for 3 hours. The solution was partitioned between 0.1 N aqueous HCl (5 mL) and dichloromethane (10 mL). The aqueous layer was extracted with dichloromethane (2×10 mL) and the organic layers were combined, dried (Na$_2$SO$_4$) and concentrated. The resulting carboxylic acid was used directly in the next step.

Trifluoroacetic acid (6.4 mL) was added dropwise to a solution of the carboxylic acid in dichloromethane (4.2 mL) at 0° C. The reaction mixture was warmed to room temperature and stirred for 3 hour. The solution was concentrated by coevaporation with toluene (3×5 mL) and the resulting ammonium salt was used directly in the next step.

Diisopropylethylamine (62 µL, 0.37 mmol) and TBTU (60 mg, 0.19 mmol) were added successively to a solution of the linear peptide and 1-hydroxybenzotriazole (25 mg, 0.19 mmol) in dichloromethane (145 mL) at room temperature. The reaction mixture was stirred for 3 days. The reaction mixture was concentrated under reduced pressure. The residue was purified by column chromatography (dichloromethane with 0.5 to 4% methanol) to give macrocyclus 27 as a sticky solid (36 mg, 40 µmol, 43%).

HRMS (ESI) calculated for C$_{44}$H$_{52}$N$_{10}$O$_9$S ([M]$^+$): 897.3718, found 897.3719.

Argyrin F (3)

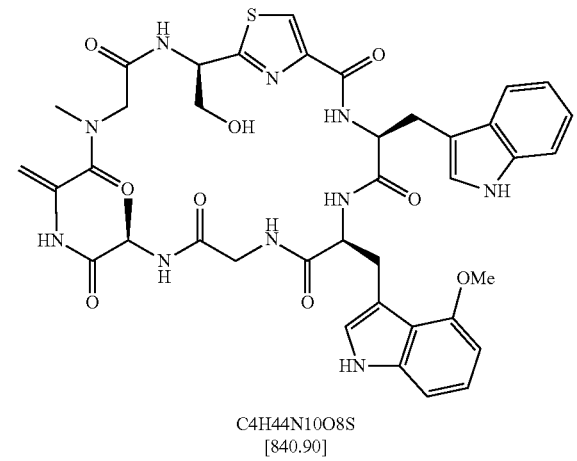 [SMILES: C=C1NC(=O)[C@@H](C)NC(=O)CNC(=O)[C@H](Cc2c[nH]c3cccc(OC)c23)NC(=O)[C@H](Cc2c[nH]c3ccccc23)NC(=O)c2csc(n2)[C@@H](CO)NC(=O)CN(C)C1=O]

C4H44N10O8S
[840.90]

Trifluoroacetic acid (0.5 mL) was added dropwise to a solution of cyclic peptide 27 (5 mg, 5.6 µmol, 1 eq.) in CH$_2$Cl$_2$ (1 mL) at 0° C. The reaction mixture was warmed to room temperature and stirred for 3 days. The solution was concentrated by coevaporation with toluene (3×5 mL). The residue was purified by column chromatography (CH$_2$Cl$_2$ with 0.5-10% MeOH) to give Argyrin F (3) as a sticky solid (2.7 mg, 3 µmol, 58% yield).

$^1$H-NMR (400 MHz, CDCl$_3$): δ=1.07 (dd, J=17.5 and 5.17 Hz, 1 H), 1.40 (d, J=7 Hz, 3 H), 2.85 (dd, J=15.3 and 3.18 Hz, 1 H), 3.16 (s, 3 H), 3.31 (dd, J=14.9 and 3.8 Hz, 1 H), 3.43 (d, J=16.5, 1 H), 3.54-3.47 (m, 3 H), 4.09-4.03 (m, 1 H), 4.21-4.18 (m, 1 H), 4.33-4.24 (m, 3 H), 4.34 (s, 3 H), 4.49-4.44 (m, 1 H), 4.79 (d, J=1.19 Hz, 1 H), 4.99 (d, J=16.5 Hz, 1 H), 5.08-5.04 (m, 1 H), 5.09 (d, J=1.6 Hz, 1 H), 5.38 (d, J=7.95 Hz, 1 H), 5.55-5.50 (m, 1 H), 6.33 (t, J=7.05 Hz, 1 H), 6.81 (d, J=2.38 Hz, 1 H), 6.91-6.84 (m, 1 H), 6.92 (d, J=4.37 Hz, 1 H), 7.05 (d, J=8.15 Hz, 2 H), 7.35-7.28 (m, 2 H), 8.10 (s, 1 H), 8.33 (d, J=1.99 Hz, 1 H), 8.36 (d, J=8.74 Hz, 1 H), 8.54 (d, J=7.35 Hz, 1 H), 8.77 (d, J=1.59 Hz, 1 H), 9.72 (s, 1 H), 10.67 (s, 1 H) ppm.

$^{13}$C-NMR (100 MHz, CDCl$_3$): δ=13.8, 14.2, 22.8, 26.9, 27.0, 37.8, 40.6, 48.7, 51.4, 51.5, 52.1, 56.2, 57.7, 64.0, 101.4, 101.4, 106.0, 106.7, 108.4, 111.4, 116.2, 117.4, 119.4, 121.4, 123.6, 123.7, 123.8, 125.3, 126.6, 129.7, 133.4, 134.7, 136.3, 138.4, 150.6, 152.4, 159.7, 167.2, 167.9, 168.5, 170.1 ppm.

HRMS (ESI) calculated for C$_{40}$H$_{44}$N$_{10}$O$_9$S ([M]$^+$): 841.3092, found 841.3087.

4. New Argyrine-Derivatives—Functional Assays

Cells and Tissue Culture

Primary human fibroblasts (HKI); HCT116 (colon cancer), MCF7 (breast cancer), CaCo (colon cancer), A549 (Lung cancer), HeLa (cervical cancer) and immortalized MEFs were cultivated in DMEM supplemented with 5% FCS and 2 mg/ml penicillin/streptomycin. SW480 cells (colon cancer) were cultivated in MC Coy's media supplemented with 5% FCS and 2 mg/ml penicillin/streptomycin.

Antibodies, Western Blotting, Immunofluorescence, Immunohistochemistry

Immunohistochemical staining of mouse tumor tissue, western Blotting and immunofluorescence experiments were done as previously described (Timmerbeul, I. et al. Testing the importance of p27 degradation by the SCFskp2 pathway in murine models of lung and colon cancer. *Proc Natl Acad Sci USA* 103, 14009-14 (2006). Kossatz, U. et al. C-terminal phosphorylation controls the stability and function of $p27^{kip1}$. *Embo J* 25, 5159-70 (2006).). The following antibodies were used: p27 (Cat. No. K25020-150 ; Transduction Labs), p21 (N20; Santa Cruz), p53 (FL-393; Santa Cruz), NfKB (C-20; Santa Cruz), Bax (P-19; Santa Cruz), Alexa fluor 488 (#A11001; Invitrogen), 20S-proteasome subunit beta 2 (Z) (PW9300; Biomol, for human cells), 20S-proteasome subunit beta 2 (Z) (PW8145; BIO TREND, for mouse cells); 20S proteasome subunit beta 1(Y) (PW8140; BIO TREND), 20S proteasome subunit beta 5 (PW8895; BIO TREND) ; PECAM Antibody clone MEC 13.3 (#550274; BD Pharmingen).

MTT Assays, Apoptosis, Flow Cytometry

MTT assays were done as previously described (Sasse, F. et al. Argyrins, immunosuppressive cyclic peptides from myxobacteria. I. Production, isolation, physico-chemical and biological properties. *J Antibiot (Tokyo)* 55, 543-51 (2002)). TUNEL staining of tissue sections was performed on 10 micrometer sections which were deparafinised and treated as recommended by the manufacturer. (In Situ Cell Death Detection Kit, Fluorescein; ROCHE, Cat #11 684 795 910). Flow cytometric analysis of cultured cells was done using a Becton Dickinson fluorescence cytometer as previously described (Malek, N.P. et al. A mouse knock-in model exposes sequential proteolytic pathways that regulate $p27^{Kip1}$ in G1 and S phase. *Nature* 413, 323-7 (2001)). Analysis of the distribution of cells in the cell cycle and the sub-G1 fraction was done using Cell Quest software. A histone-associated-DNA-fragments ELISA was used to determine the number of apoptotic cells according to manufacturers instructions (Roche #11 774425001).

Proteasome Purification, Proteasome Assays

Proteasome assays with purified 20S proteasome were performed as previously described (Lightcap, E. S. et al. Proteasome inhibition measurements: clinical application. *Clin Chem* 46, 673-83 (2000)) using erythrocyte-derived 20S proteasome (Biomol International,#LP PW8720) and fluorometric substrates Succ-LLVY-AMC, BZ-VGR-AMC and Z-Lle-AMC (Biomol International, LP PW9905) as probes according to the manufacturers instructions. Proteasome extraction from cells and tumor sections was done as previously described (Crawford, L. J. et al. Comparative selectivity and specificity of the proteasome inhibitors BzLLLCOCHO, PS-341, and MG-132. *Cancer Res* 66, 6379-86 (2006)). Briefly cells (MEF or MCF-7) or tissue sample homogenate (tumor sections) were re-suspended in 1 mL ATP/DTT lysis buffer (10 mmol/L Tris-HCl (pH7.8), 5 mmol/L ATP, 0.5 mmol/L DTT, 5 mmol/L $MgCl_2$), and incubated on ice for 10 minutes, followed by sonication for 15 seconds. The lysates were centrifuged at 400×g for 10 min at 4° C., and the resulting supernatant containing proteasomes was stable at −80° C. with the addition of 20% glycerol for at least 1 month. Protein concentration of the samples was measured using a coomassie protein assay (Pierce, Rockford, Ill.).

For proteasome extraction from whole blood, frozen whole blood cell pellets were thawed and lysed in 2-3 pellet volumes cold lysis buffer (5 mM EDTA, pH 8.0). Lysates were spun down at 4° C. and the supernatant was transferred to a fresh tube. 5 µl was taken for the determination of protein concentration using a coomassie protein assay (Pierce, Rockford, Ill.).

Proteasome assays using proteasome purified from cells or tissues were carried out in a 100 µL reaction volume containing 20 µg proteasome extract, 50 mmol/L EDTA and 60 µmol/L fluorogenic substrate (chymotrypsin-like(CT-L), trypsin-like(T-L) or caspase-like (C-L)) in ATP/DTT lysis buffer at 37° C. The assay buffer was supplemented with a final concentration of 0.05% SDS for the evaluation of the chymotrypsin-like activity and caspase-like activity. The rate of cleavage of fluorogenic peptide substrates was determined by monitoring the fluorescence of released amonomethylcoumarin using a Victor 1420 Multilabel counter (Wallac) at an excitation wavelength of 395 nm and emission wavelength of 460 nm over a period of 60 min.

HMVEC Culture, in vitro Capillary-Like Tube Structure Formation Assay and Immunofluorescence Primary microvascular endothelial cells (HMVEC) were isolated from human foreskin. The cells were kept at 37° C. and 10% CO2 in EGM-2 MV from Cambrex which includes the basal medium (EBM-2), FBS, hydrocortisone, hFGF-B, VEGF, R3-IGF, ascorbic acid, hEGF, gentamicin and amphotericin. The effect of argyrin A or bortezomib on in vitro angiogenesis was determined by matrigel capillary-like tube structure formation assay. To examine the effect of the different compounds on in vitro angiogenesis, HMVECs were seeded in 96-well culture plates precoated with Matrigel (BD Biosciences, #354248) and exposed to argyrin A or bortezomib. Enclosed networks of tube structures from three randomly chosen fields were scored under the microscope (Leica, Cambridge, United Kingdom). Pictures were taken with an Axio Vision 3.1 Zeiss camera and scored by determining tube length and the formation of closed vessel like structures.

Xenotransplant Studies $1 \times 10^7$ SW480 cells or HCT116 cells (in 100 microliters DMEM medium and 100 microliters matrigel) were s.c. injected into the flanks of NMRI nu/nu mice. Tumours grew for approx. 18 days until they reached appropriate size (200 mm3). Tumour size was measured with a digital calliper and calculated with the help of the following formula: (Length× width2)*π/6. All experiments were done after review and in accordance with the animal rights and protection agencies of Lower Saxony, Germany.

EM

Small specimens of the tumor were fixed in 2.5% glutaraldehyde (Polysciences, Warrington, Pa., USA) in 0.1 M sodium cacodylate, pH 7.3 and post-fixed with 2% osmium tetroxide (Polysciences) in the same buffer. After dehydration in graded alcohols they were embedded in Epon (Serva, Heidelberg, Germany). Thin sections stained with uranyl acetate and lead citrate were examined in a Philips EM 301 electron microscope. The electron micrographs were selected, digitalized, and processed using Adobe Photoshop 6.0.

Effect of Different Argyrin-Derivatives

The following table summarizes the effects of argyrin-derivatives B and F on two cancer cell lines, H15 (cervix carcinoma) and SW-480 (colon cancer). In order to test the efficacy, a p27-GFP-clone was used.

| Argyrin | Mean of FSC-H (Log)* H15 p27-GFP-clone | MIC (visual)** [µg/ml] H15 | MIC (visual)** [µg/ml] SW-480 | IC-50*** [µg/ml] SW-480 |
|---|---|---|---|---|
| B | 7.60 | 12 | 12 | Ca. 0.05 |
| F | 11.24 | 0.5 | 0.2 | 0.05 |

*The GFP-fluorescence was determined per FACS after a 24 h incubation of the clone H15GFP-p27 (HeLa-cell line; cervix-carcinoma) with the different argyrin-derivatives (500 ng/ml).
**Minimal concentration of a serial dilution exhibiting a visual effect.
***Half-maximal inhibition of the proliferation of SW-480 (colon cancer cell line; analysis following an MTT-test). It can be seen that both argyrin B and F are effective.

The following derivatives have been generated:

(30)

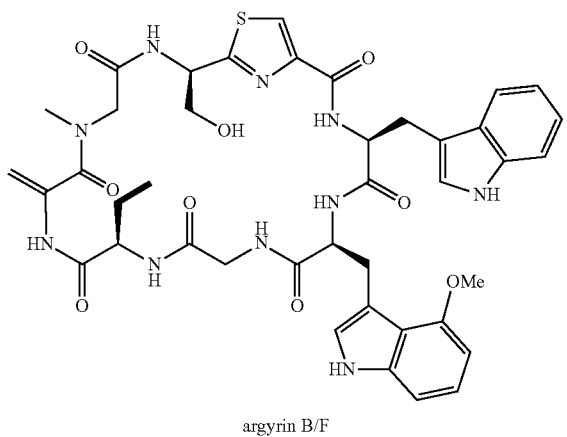

argyrin B/F

This derivative is a "hybrid" of the structures of argyrin B and F (for an example for the synthesis, see above), and it is therefore expected to share the pharmaceutical characteristics with the group of argyrins, including a beneficial effect on conditions, such as the induction of immunotolerance, autoimmune diseases, bacterial infections, and proliferative diseases, such as cancers.

Further preliminary experiments indicate that furthermore the pharmacokinetic properties of the argyrins can be modified by choosing an argyrine-derivative showing the configurations as indicated below. It is expected that a stabilization of the overall conformation of the molecule also improves the bioavailability of the molecule for the patient to be treated.

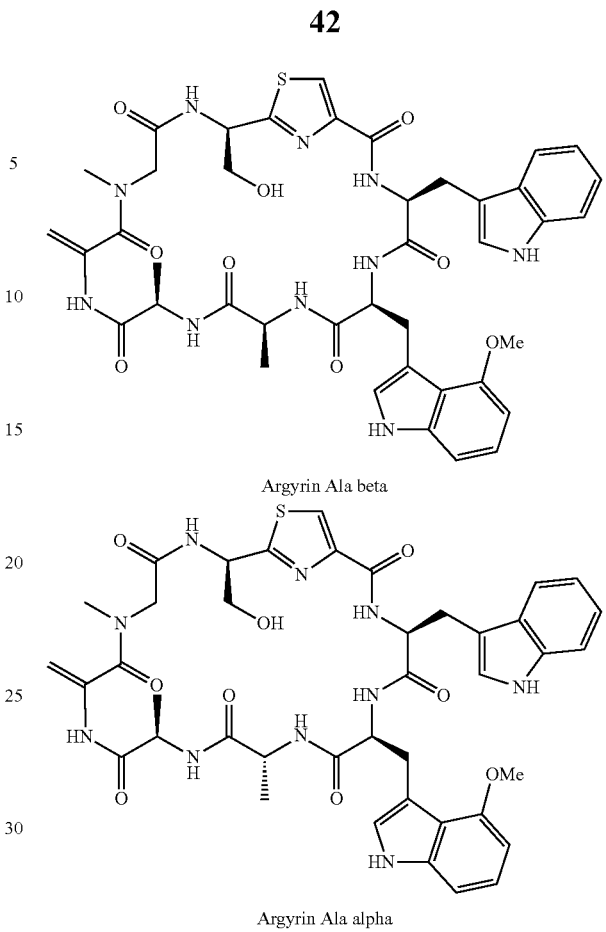

Argyrin Ala beta

Argyrin Ala alpha

Proteasome Purification, Proteasome Assays

Proteasome assays with purified 20S proteasome were performed as previously described (Lightcap et al., 2000) using erythrocyte-derived 20S proteasome (Biomol International,#LP PW8720) and fluorometric substrates Succ-LLVY-AMC, BZ-VGR-AMC and Z-Lle-AMC (Biomol International, LP PW9905). Proteasome extraction from cells and tumor sections was done as previously described (Crawford et al., 2006). For proteasome extraction from whole blood, frozen whole blood cell pellets were thawed and lysed in 2-3 pellet volumes cold lysis buffer (5 mM EDTA, pH 8.0). Lysates were spun down at 4° C. and the supernatant was transferred to a fresh tube. 5 µl was taken for the determination of protein concentration using a coomassie protein assay (Pierce, Rockford, Ill.). Proteasome assays using proteasome purified from cells or tissues were carried out in a 100 µL reaction volume containing 20 µg proteasome extract, 50 mmol/L EDTA and 60 µmol/L fluorogenic substrate (chymotrypsin-like(CT-L), trypsin-like(T-L) or caspase-like (C-L)) in ATP/DTT lysis buffer at 37° C. The assay buffer was supplemented with a final concentration of 0.05% SDS for the evalution of the chymotrypsin-like activity and caspase-like activity. The rate of cleavage of fluorogenic peptide substrates was determined by monitoring the fluorescence of released aminomethylcoumarin using a Victor 1420 Multilabel counter (Wallac) at an excitation wavelength of 395 nm and emission wavelength of 460 nm over a period of 60 min.

Apoptosis Assay

Histone-associated-DNA-fragmentation was done according to the manufacturer's instructions (Roche #11 774425001)

The following results were obtained with the compounds as indicated:

20S-Proteasome-Test (Manual)

| Substance | Plate | Substrate | Stock solution used µg/ml | Conc. in test µmol/L | rel. activ. in % after 20 min. |
|---|---|---|---|---|---|
| Argyrin F | 019 | chymotrypsin-like | 1000 | 200 | 15 |
| Argyrin ala beta | | chymotrypsin-like | 1000 | 100 | 8 |
| Argyrin ala alpha | | chymotrypsin-like | 1000 | 100 | 17 |
| Argyrin F | 020 | trypsin-like | 1000 | 200 | 32 |
| Argyrin ala beta | | trypsin-like | 1000 | 100 | 26 |
| Argyrin ala alpha | | trypsin-like | 1000 | 100 | 72 |
| Argyrin F | 021 | caspase-like | 1000 | 200 | 17 |
| Argyrin ala beta | | caspase-like | 1000 | 100 | 7 |
| Argyrin ala alpha | | caspase-like | 1000 | 100 | 11 |

It can be seen that the preferred derivatives Argyrin ala alpha and particularly Argyrin ala beta have higher activities than Argyrin F. Thus, both the modified positions and the conformations play a decisive role for the activity of these compounds, and the argyrins in general.

The invention claimed is:
1. A method for producing a macrocycle compound, wherein reaction steps of the method are shown by the following general scheme:

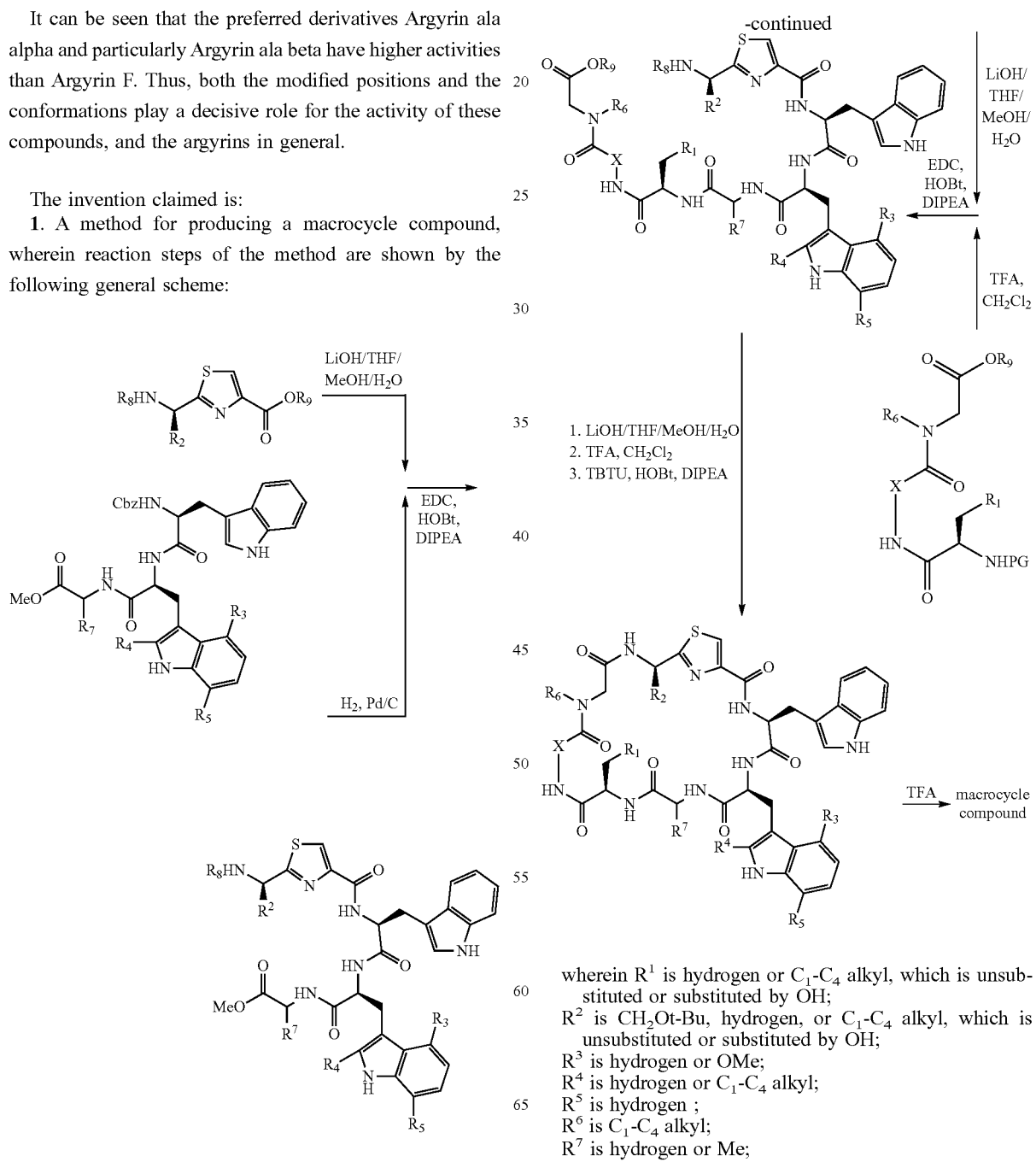

wherein $R^1$ is hydrogen or $C_1$-$C_4$ alkyl, which is unsubstituted or substituted by OH;
$R^2$ is $CH_2Ot$-Bu, hydrogen, or $C_1$-$C_4$ alkyl, which is unsubstituted or substituted by OH;
$R^3$ is hydrogen or OMe;
$R^4$ is hydrogen or $C_1$-$C_4$ alkyl;
$R^5$ is hydrogen ;
$R^6$ is $C_1$-$C_4$ alkyl;
$R^7$ is hydrogen or Me;

$R^8$ is hydrogen or Boc;
$R^9$ is hydrogen or Et;
X is $C=CH_2$; and
PG is a protecting group,
wherein the method is performed without enzymatic resolution.

2. The method, according to claim 1, wherein the PG is selected from the group consisting of: Boc, Fmoc, and Cbz.

3. The method for producing a macrocycle compound according to claim 1, wherein said macrocycle compound is selected from an argyrin A to F.

4. The method for producing a macrocycle compound according to claim 1, wherein the synthesis comprises solid phase peptide synthesis.

5. The method for producing a macrocycle compound according to claim 1, wherein said macrocycle compound is selected from the following formulae:

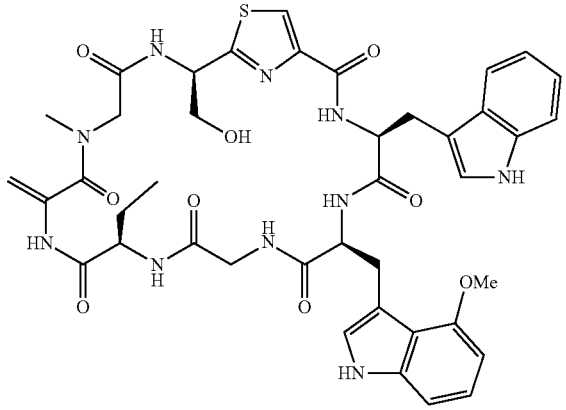

Argyrin B/F,

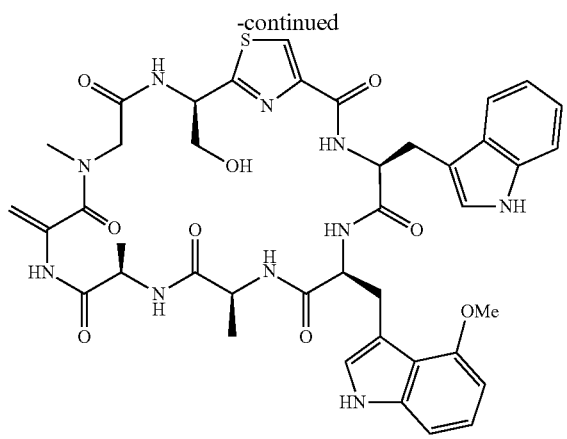

Argyrin Ala beta, or

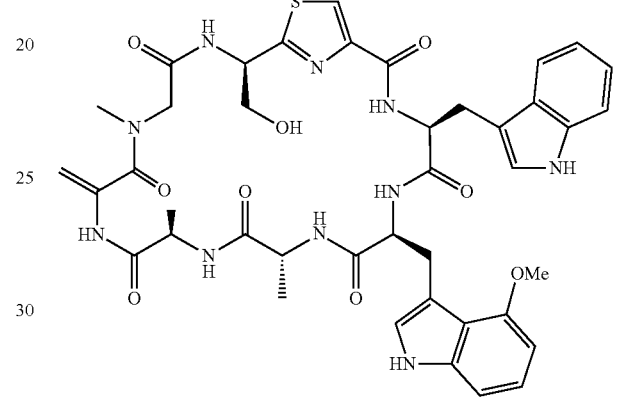

Argyrin Ala alpha.

* * * * *

UNITED STATES PATENT AND TRADEMARK OFFICE
CERTIFICATE OF CORRECTION

PATENT NO.       : 9,458,200 B2
APPLICATION NO.  : 13/000516
DATED            : October 4, 2016
INVENTOR(S)      : Markus Kaleese et al.

It is certified that error appears in the above-identified patent and that said Letters Patent is hereby corrected as shown below:

In the Specification

Column 13,
Line 66, "J=3.1 hz," should read --J=3.1 Hz,--.

Column 14,
Line 48, "($_{[M+Na]}$$^+$):" should read --([M+Na]$^+$):--.

Column 15,
Line 59, "fil-tered" should read --filtered--.

Column 22,
Line 25, "4.55" should read --4.45--.

Column 25,
Line 64, " $[\alpha]_D^{20}=55.9$ " should read -- $[\alpha]_D^{20}=55.9$ --.

Column 28,
Line 30, " $[\alpha]_{598}^{20}=14.21$ " should read -- $[\alpha]_{598}^{20}=14.21$ --.

Column 28,
Line 37, "([M$^+$) requires" should read --([M]$^+$) requires--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,458,200 B2

Column 29,
Line 44, "...-OMe (23)" should read --...OMe (23):--.

Column 41,
Line 24, "HIS" should read --HI5--.